US009193970B1

(12) United States Patent
Gupte

(10) Patent No.: US 9,193,970 B1
(45) Date of Patent: Nov. 24, 2015

(54) REPLICATION FACTOR C-40 (RFC40/RFC2) AS A PROGNOSTIC MARKER AND TARGET IN ESTROGEN POSITIVE AND NEGATIVE AND TRIPLE NEGATIVE BREAST CANCER

(71) Applicant: Rakhee S. Gupte, Fishkill, NY (US)

(72) Inventor: Rakhee S. Gupte, Fishkill, NY (US)

(73) Assignee: Raadysan Biotech, Inc., Fishkill, NY (US)

( * ) Notice: Subject to any disclaimer, the term of this patent is extended or adjusted under 35 U.S.C. 154(b) by 0 days.

(21) Appl. No.: 14/204,639

(22) Filed: Mar. 11, 2014

Related U.S. Application Data

(60) Provisional application No. 61/782,901, filed on Mar. 14, 2013.

(51) Int. Cl.
C12N 15/11 (2006.01)
C12N 15/113 (2010.01)
C12Q 1/68 (2006.01)
G01N 33/574 (2006.01)

(52) U.S. Cl.
CPC ............ *C12N 15/113* (2013.01); *C12Q 1/6886* (2013.01); *G01N 33/57415* (2013.01); *C12N 2310/14* (2013.01); *C12N 2310/141* (2013.01); *C12N 2320/10* (2013.01); *C12N 2320/30* (2013.01); *C12Q 2600/112* (2013.01); *C12Q 2600/158* (2013.01)

(58) Field of Classification Search
USPC .......................... 536/23.1, 24.3, 24.5; 514/44
See application file for complete search history.

(56) References Cited

U.S. PATENT DOCUMENTS 8,455,199 B2 * 6/2013 Marsh et al. ................. 435/6.14

OTHER PUBLICATIONS

Gupte, et al., The Second Subunit of the Replication Factor C complex (RFC40) and the Regulatory Subunit (RIα) of Protein Kinase A Form a Protein Complex Promoting Cell Survival, Cell Cycle, vol. 4, Issue 2, pp. e64-e70, Feb. 2005.
Gupte, et al., RIα Influences Cellular Proliferation in Cancer Cells by Transporting RFC40 into the Nucleus, Cancer Biology & Therapy, vol. 4, Issue 4, pp. 429-437, Apr. 2005.
Gupte, et al., Cyclic AMP Regulates the Expression and Nuclear Translocation of RFC40 in MCF7 Cells, Experimental Cell Research, vol. 312, Issue 6, pp. 796-806, Jan. 17, 2006.
Gupte, et al., Phosphorylation of RIα by Cyclin-Dependent Kinase CDK 2/Cyclin E Modulates the Dissociation of the RIα-RFC40 Complex, Cell Cycle, vol. 5, Issue 6, pp. 653-660, Mar. 16, 2006.
Ata, et al., Down-Regulation of Replication Factor C-40 (RFC40) Causes Chromosomal Missegregation in Neonatal and Hypertrophic Adult Rat Cardiac Myocytes, PLoS One, vol. 7, Issue 6, e39009, pp. 1-12, Jun. 2012.
Karnani, et al., Nuclear Localization of RFC40 by RIα: A Link between Cellular Signaling and Proliferation, Cancer Biology & Therapy, vol. 4, Issue 4, pp. 438-439, Apr. 2005.

* cited by examiner

*Primary Examiner* — Terra C Gibbs
(74) *Attorney, Agent, or Firm* — Hodgson Russ LLP

(57) ABSTRACT

The present disclosure relates generally to cancer and particularly to breast cancer including estrogen sensitive, estrogen resistant and triple negative breast cancer (TNBC), and to methods of diagnosis and prognosis thereof and therapeutic intervention involving replication factor C 40 (RFC40). Methods and assays for evaluating breast cancer are provided. The disclosure also relates to inhibition or modulation of RFC40 in treatment or alleviation of cancer, including breast cancer. RFC40 inhibitors, including siRNAs and miRNAs, which specifically affect cancer cells, particularly breast cancer cells, are provided.

6 Claims, 26 Drawing Sheets

A

B
RFC40 Protein (SEQ ID NO:1)
Accession/UniProtKB/Swiss-Prot: P35250.3

```
  1 MEVEAVCGGA GEVEAQDSDP APAFSKAPGS AGHYELPWVE KYRPVKLNEI VGNEDTVSRL
 61 EVFARSGNVP NIIIAGPPGT GKTTSILCLA RALLGPALKD AMLELNASND RGIDVVRNKI
121 KMFAQQKVTL PKGRHKIIIL DEADSMTDGA QQALRRTMEI YSKTTRFALA CNASDKIIEP
181 IQSRCAVLRY TKLTDAQILT RLMNVIEKER VPYTDDGLEA IIFTAQGDMR QALNNLQSTF
241 SGFGFINSEN VFKVCDEPHP LLVKEMIQHC VNANIDEAYK ILAHLWHLGY SPEDIIGNIF
301 RVCKTFQMAE YLKLEFIKEI GYTHMKIAEG VNSLLQMAGL LARLCQKTMA PVAS
```

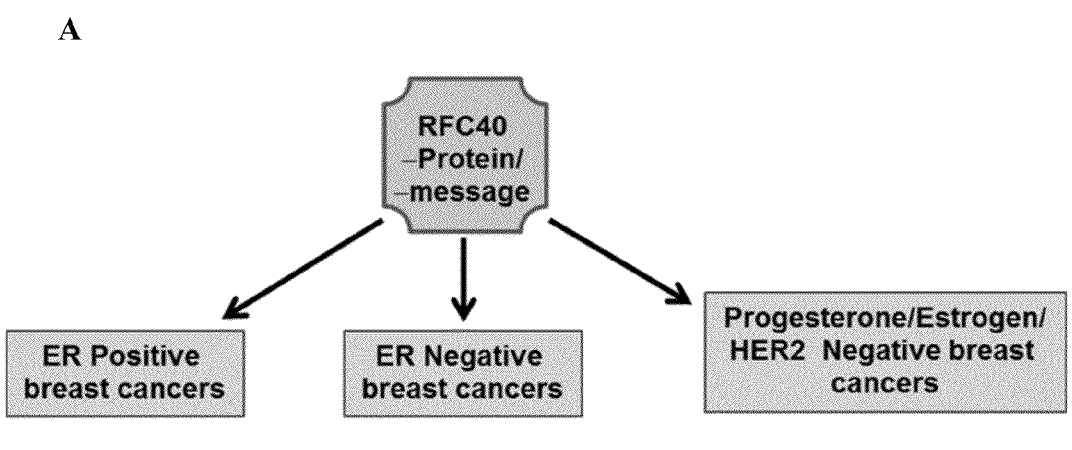

B

RFC40 Protein (SEQ ID NO:1)
Accession/UniProtKB/Swiss-Prot: P35250.3

```
  1 MEVEAVCGGA GEVEAQDSDP APAFSKAPGS AGHYELPWVE KYRPVKLNEI VGNEDTVSRL
 61 EVFAREGNVP NIIIAGPPGT GKTTSILCLA RALLGPALKD AMLELNASND RGIDVVRNKI
121 KMFAQQKVTL PKGRHKIIIL DEADSMTDGA QQALRRTMEI YSKTTRFALA CNASDKIIEP
181 IQSRCAVLRY TKLTDAQILT RLMNVIEKER VPYTDDGLEA IIFTAQGDMR QALNNLQSTF
241 SGFGFINSEN VFKVCDEPHP LLVKEMIQHC VNANIDEAYK ILAHLWHLGY SPEDIIGNIF
301 RVCKTFQMAE YLKLEFIKEI GYTHMKIAEG VNSLLQMAGL LARLCQKTMA PVAS
```

FIGURE 2
A
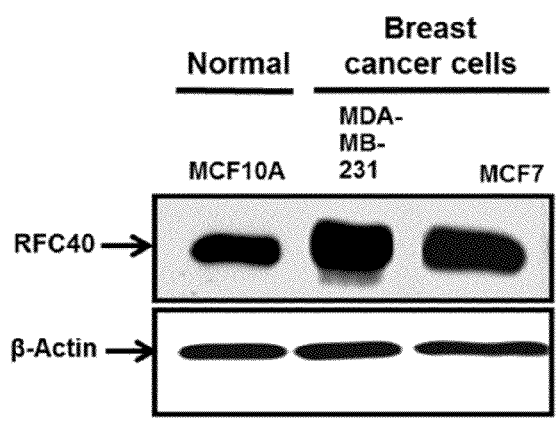
B
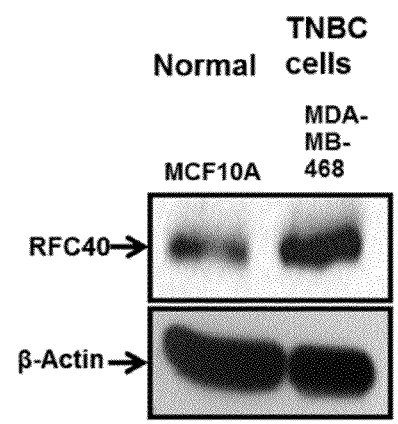

FIGURE 4
A
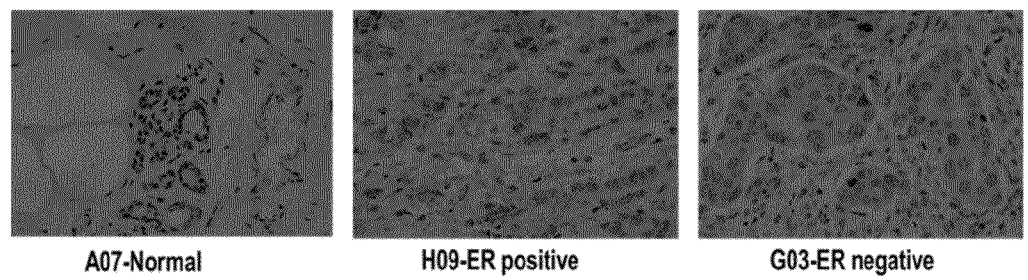
B
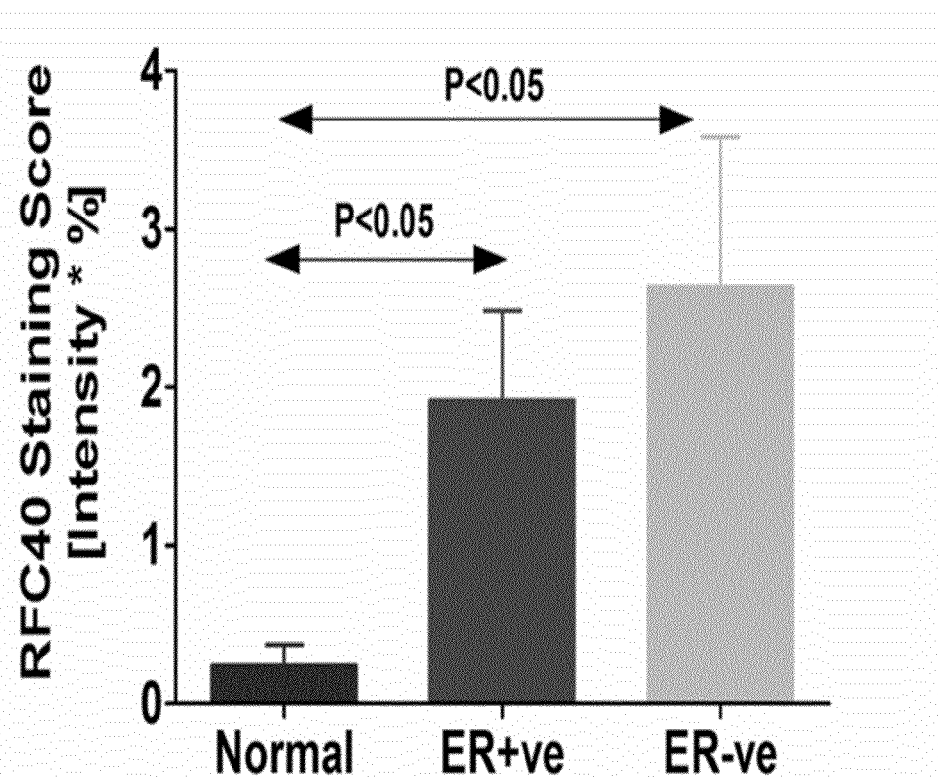

FIGURE 7
A
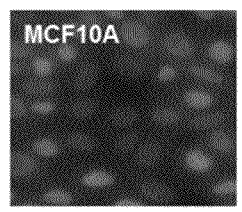 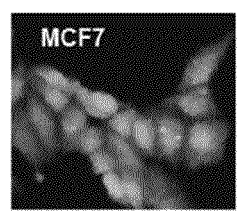 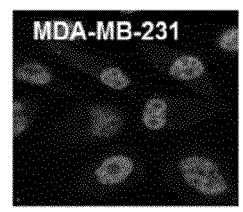

FIGURE 18

On-Targetplus SMARTpool RFC40-SiRNA

Human RFC40 mRNA (cDNA): (SEQ ID NO:2)

```
atgga ggtggaggcc gtctgtggtg gcgcgggcga ggtggaggcc caggactctg
accctgcccc tgccttcagc aaggcccccg gcagcgccgg ccactacgaa ctgccgtggg
ttgaaaaata taggccagta aagctgaatg aaattgtcgg gaatgaagac accgtgagca
ggctagaggt ctttgcaagg gaaggaaatg tgcccaacat catcattgcg ggccctccag
gaaccggcaa gaccacaagc attctgtgct tggcccgggc cctgctgggc ccagcactcag
aagatgccat gttggaactc aatgcttcaa atgacagggg cattgacgtt gtgaggaata
aaattaaaat gtttgctcaa caaaaagtca ctcttcccaa aggccgacat aagatcatca
ttctggatga agcagacagc atgaccgacg gagcccagca agccttgagg agaaccatgg
aaatctactc taaaaccact cgcttcgccc ttgcttgtaa tgcttcggat aagatcatcg
agcccattca gtcccgctgt gcagtcctcc ggtacacaaa gctgaccgac gcccagatcc
tcaccaggct gatgaatgtt atcgagaagg agagggtacc ctacactgat gacggcctag
aagccatcat cttcacggcc cagggagaca tgaggcaggc gctgaacaac ctgcagtcca
ccttctcagg atttggcttc attaacagtg agaacgtgtt caaggtctgt gacgagcccc
acccactgct ggtaaaggag atgatccagc actgtgtgaa tgccaacatt gacgaagcct
acaagattct tgctcacttg tggcatctgg gctactacc agaagatatc attggcaaca
tctttcgagt gtgtaaaact ttccaaatgg cagaatacct gaaactggag tttatcaagg
aaattggata cactcacatg aaaatagcgg aaggagtgaa ctctcttttg cagatggcag
gcctcctggc aaggctgtgt cagaagacaa tggccccggt ggccagttag
```

ON-TARGETplus SMARTpool siRNA (RFC40-siRNA-S1):

CUUGUAAUGCUUCGGAUAA (SEQ ID NO:3)

(RFC40-siRNA-S2):

GAACUGCCGUGGGUUGAAA (SEQ ID NO:4)

(RFC40-siRNA-S3):

CGGCAAGACCACAAGCAUU (SEQ ID NO:5)

(RFC40-siRNA-S4):

GCUGUGCAGUCCUCCGGUA (SEQ ID NO:6)

Non-Targeting siRNA (NT):

UAAGGCUAUGAAGAGAUAC (SEQ ID NO: 14)

shRNA #1 ACUACGAACUGCCGUGGGUUGAAAAAUAU (SEQ ID NO:15)

shRNA#2 GUCCCGCUGUGCAGUCCUCCGGUACACAA (SEQ ID NO:16)

FIGURE 21
A    MCF10A
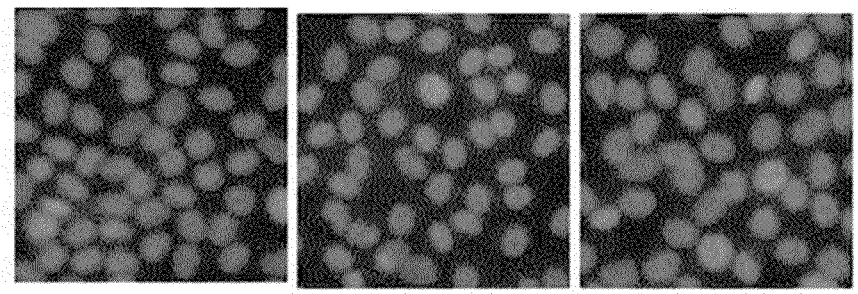
B    MDA-MB-468
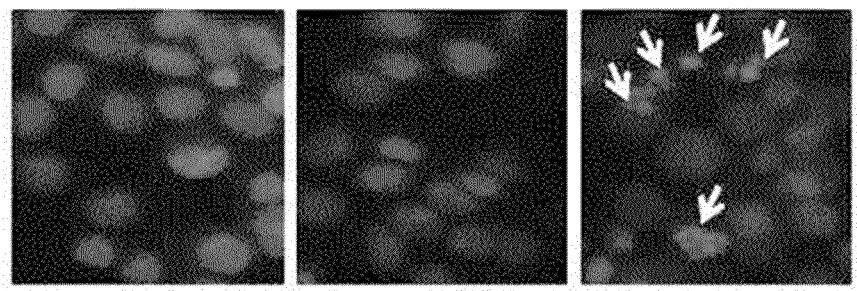

FIGURE 22
A
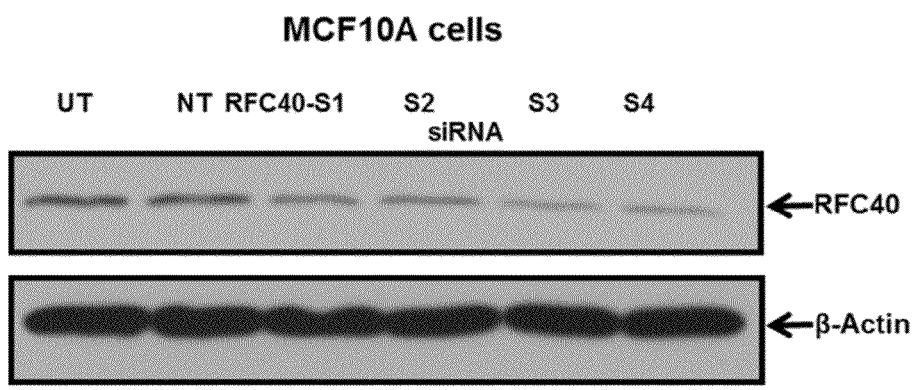
B
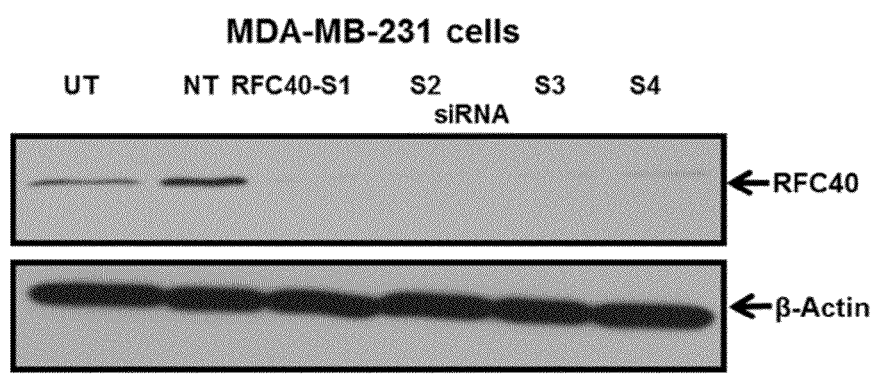

FIGURE 23
A
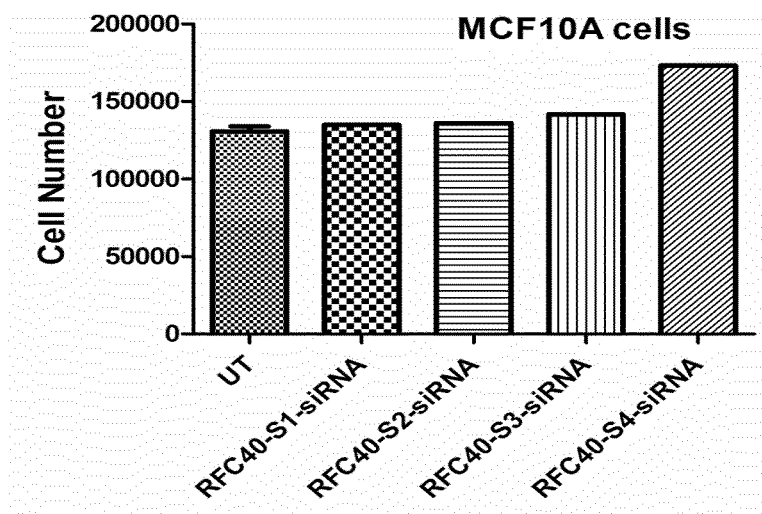
B
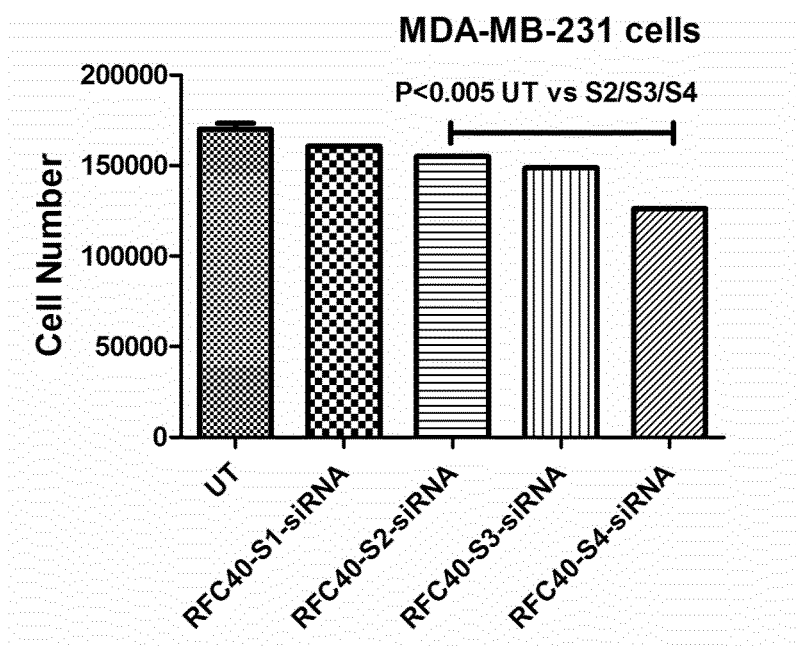

FIGURE 24

Modified miR-hsa-125a-3p Schematic

Normal as is Alignment

```
    3' ccgaggGUUCUUGGAGUGGACa 5' hsa-miR-125a-3p    mirSVR score:    -0.1347
              ||:|  :  |||||||                      PhastCons score: 0.5058
173:5' ccgaggCAGGUGGAUCACCUGa 3' RFC2
```

Modified Alignment

```
    3' ccgaggGUUCACCUAGUGGACa 5' hsa-miR-125a-3p    Modified hsa-miR-125a-3p
              ||:|||||||||||                        #1
173:5' ccgaggCAGGUGGAUCACCUGa 3' RFC2
```

```
    3' ccgaggACAAUAGGAGUGGACa 5' hsa-miR-125a-3p    Modified hsa-miR-125a-3p
                    |||||||                         #2
173:5' ccgaggCAGGUGGAUCACCUGa 3' RFC2
```

RFC2-mRNA-3'UTR is SEQ ID NO:17 miR-hsa-125-3p miRNA is SEQ ID NO:7

Modified hsa-miR-125a-3p #1 is SEQ ID NO:8

Modified hsa-miR-125a-3p #2 is SEQ ID NO:9

FIGURE 25
A
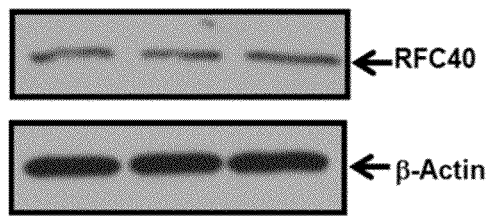
B
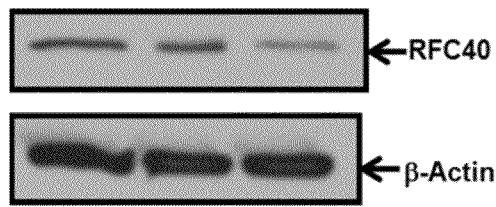

FIGURE 26
A
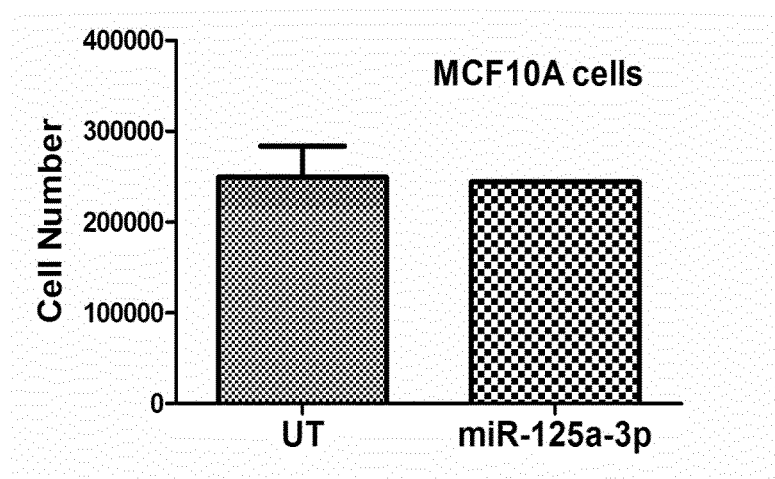
B
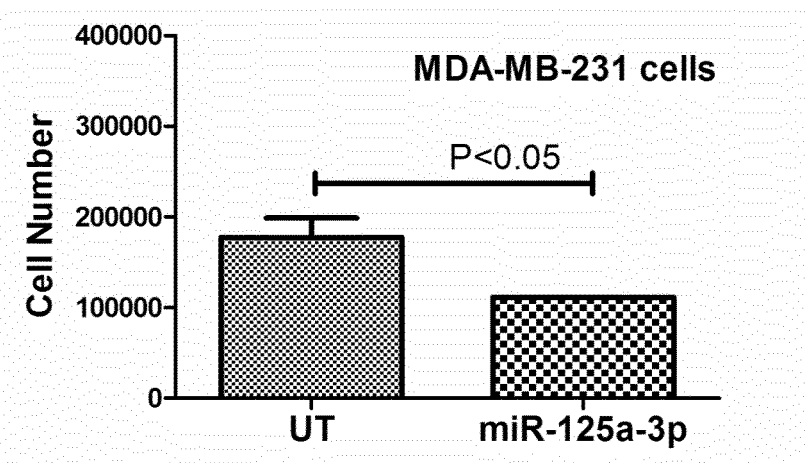

REPLICATION FACTOR C-40 (RFC40/RFC2) AS A PROGNOSTIC MARKER AND TARGET IN ESTROGEN POSITIVE AND NEGATIVE AND TRIPLE NEGATIVE BREAST CANCER

CROSS REFERENCE TO RELATED APPLICATIONS

This application claims priority to U.S. application No. 61/782,901, filed Mar. 14, 2013, the disclosure of which is incorporated herein by reference.

FIELD

The present invention relates generally to cancer and particularly to breast cancer including estrogen sensitive, estrogen resistant and triple negative breast cancer (TNBC), and to methods of diagnosis and prognosis thereof and therapeutic intervention involving replication factor C 40 (RFC40). The invention also relates to inhibition or modulation of RFC40 in treatment or alleviation of cancer, including breast cancer.

BACKGROUND OF THE INVENTION

Breast cancer accounts for 18% of all cancers in women, making it the foremost cause of cancer-related deaths in women (McPherson K et al (2000) BMJ 321(7261):624-8). Currently, routine mammography is the most commonly used method for early detection of breast cancer (Smith R A et al (2012) Oncology 26(5):471-5, 479-81, 485-6). Therefore, early diagnosis and treatment of breast cancer could play a monumental role in reducing deaths (Misek D E and Kim E H (2011) Int J Proteomics 2011:343582). Most of the drugs available for the treatment of breast cancers target growth factor and endocrine receptors, particularly the endocrine (estrogen; ER) or growth factor ((ErbB-1, ErbB-2 [human epidermal growth factor receptor 2; HER2], ErbB-3 and ErbB-4) receptors for therapy (Normanno N et al (2009) Endocr Relat Cancer 16(3):675-702).

However, emerging resistance to endocrine drugs and therapies targeted against HER2 receptors have created a dire need for identification of molecular targets that are non-receptor based and directly involved in the proliferation of the cancer cells (Normanno N et al (2005) Endocr Relat Cancer 12(4):721-47; Normanno N et al (2009) Endocr Relat Cancer 16(3):675-702). Triple Negative breast cancer (TNBC) is known to be the most aggressive of breast cancers that can metastasis beyond the breast and are more likely to recur after treatment. Tumors and cells of this subtype of breast cancer lack the estrogen, progesterone as well as the human epidermal growth factor receptor 2 and hence will not respond to the traditional therapies. Although, estrogen positive and HER2 over-expressed breast cancers have relatively good target-based agents for treatment, Triple Negative Breast cancer (TNBC) will not respond to these therapies since it lacks all these receptors. There is therefore a huge void for therapies for patients with triple-negative breast cancer (endocrine and growth receptor negative). Hence, the discovery of non receptor based target therapies that may be universally applicable to all subtypes of breast cancers is of paramount importance.

DNA replication is one of the most remarkable and challenging steps in the cell cycle and requires the collaboration of a formidable number of proteins. In eukaryotes, several accessory proteins such as Replication Factor C (RFC) and Proliferating Cell Nuclear Antigen (PCNA), confer speed and high processivity to the replicative polymerases, DNA polymerases δ (Pol δ) and ϵ. The RFC loads PCNA onto DNA and consists of five subunits, RFC140, RFC40, RFC38, RFC37 and RFC36 (Gupte R S et al (2005) Cell Cycle 4(2): 323-329). Its assembly commits the cell to DNA replication and is involved in many DNA transactions such as DNA damage checkpoint response, maintenance of genomic stability and regulation of sister chromatid cohesion in mitosis as well as in meiosis (Majka J and Burgers P M (2004) Prog Nucleic Acid Res Mol Biol 78: 227-260; Petronczki M et al (2004) J Cell Sci 117(Pt 16): 3547-3559).

Amongst all the RFC subunits, only the second subunit, RFC40/RFC2 can independently unload PCNA and inhibit DNA Pol δ activity (Cai J et al (1997) J Biol Chem 272(30): 18974-81; Pan Z Q et al (1993) Proc Natl Acad Sci USA 90(1):6-10). It has been recently discovered that RFC40 is required for accurate chromosomal segregation and completion of cell division after mitosis in proliferating neonatal rat cardiac myocytes, suggesting a role for RFC40 in mitosis and cytokinesis (Ata H et al (2012) PLoS One 7(6):e39009). Additionally, it was also observed that inhibition of endogenous RFC40 in proliferating neonatal rat cardiac myocytes causes cell death (Ata H et al (2012) PLoS One 7(6):e39009). Consistently, it has been demonstrated that deletion of RFC40 gene is embryonically lethal in yeast (Cullmann G et al (1995) Mol Cell Biol 15(9):4661-71). Also, halo-insufficiency of RFC40 causes growth retardation in Williams-Beurner syndrome (Peoples R et al (1996) Am J Hum Genet 58:1370-3). Taken together these findings suggest that RFC40 is essential for cell proliferation.

Interaction between the second subunit of the Replication Factor C, RFC40, and the regulatory subunit of Protein Kinase A, RIα, has been identified using yeast two-hybrid screening (Gupte R S et al (2005) Cell Cycle 4(2): 323-329). This complex has been shown to be essential for cell survival and that RIα functions as a nuclear transport protein for RFC40 via its non-conventional nuclear localization sequence (NLS) (Gupte R et al (2005) Cancer Biology and Therapy 4(4):429-437). Moreover, deletions in the RFC40 binding region on RIα, or either deletion or mutations of the non-conventional NLS of RIα, leads to G1 arrest, suggesting that the RIα-RFC40 complex is transported to the nucleus at the G1/S transition. Additionally, elevated intracellular cAMP levels exert transcriptional/post-transcriptional effects on mRNA levels and a translation effect on the protein expressions of both RFC40 and RIα, thereby increasing the amount of the RIα-RFC40 complex formation and hence promoting the nuclear transport of RFC40 by RIα (Gupte R et al (2006) Exper Cell Res 312:796-806).

Currently there clearly is a need for molecular targets that are non-receptor based for use and application towards the development of drug therapies for breast cancers lacking endocrine and growth receptors such as triple negative breast cancers (TNBC) and for therapies which are endocrine and growth factor receptor independent and therefore applicable to all or most forms of breast cancer. The present invention provides a novel independent marker and target for cancer diagnosis and therapy, particularly including breast cancer.

The citation of references herein shall not be construed as an admission that such is prior art to the present invention.

SUMMARY OF THE INVENTION

In one aspect, the present invention extends to the diagnosis and/or treatment of breast cancer in mammals, particularly in humans, using replication factor C 40 (RFC40) and particularly to RFC40 protein and/or gene expression as a marker in breast cancer and to RFC40 as a novel and specific oncologic target for intervention in cancer, particularly in breast cancer, including estrogen sensitive, estrogen resistant and triple negative breast cancer (TNBC).

The invention extends to applications in and diagnosis, prognosis, and/or treatment of breast hyperplasia, pre-neoplastic lesions and/or ductal carcinoma I situ (DCIS).

In particular, the DNA replication protein, RFC40, is presently identified and validated as a non-receptor based molecular marker and specific target for breast cancer, irrespective of its receptor status, including TNBC. The studies provided herein establish that RFC40 protein and messenger RNA encoding it, as well as RFC40 gene copy numbers, are increased in breast cancers, including in estrogen sensitive, estrogen resistant and TNBC. The present studies demonstrate that inhibition or modulation of RFC40 such that its activity or expression is reduced or blocked results in reduction in cell numbers and inhibition of cell proliferation or division in estrogen positive (ER positive), estrogen negative (ER negative), and progesterone, estrogen and human epidermal growth factor receptor 2-HER2 negative or TNBC cells. Thus, RFC40 provides a non-receptor diagnostic and prognostic marker and a therapeutic or interventional target involved in cell division and proliferation which, without intending to be constrained by theory, is independent of growth factor and endocrine receptor status. Inhibition or modulation of RFC40 is therefore applicable in early stage breast cancer, late stage breast cancer, on drug failure or resistance to receptor-based therapies, and in instances of recurrence.

In accordance with the present invention, methods for the treatment of breast cancer and/or the reduction of risk for breast cancer by modulating RFC40, particularly via inhibitors specifically directed against RFC40, including siRNAs or miRNAs, are provided. In an aspect of the method, the treatment of breast cancer is provided comprising modulating RFC40 expression or activity in cells, particularly and specifically in oncogenic or cancer cells versus normal or benign cells, particularly non-cancerous breast cells.

The invention thus provides a method of inhibiting the growth and/or cell division of cancer cells, said method comprising contacting a population of mammalian cells comprising cancer cells with an inhibitor of the activity or expression of RFC40.

In an aspect of the method, the cancer cells are breast cancer cells. In a further aspect of the method, the breast cancer cells are estrogen positive, estrogen negative or progesterone/estrogen/HER2 negative breast cancer cells (TNBCs).

The method includes inhibitors of RCF40 expression and/or activity, and compositions comprising such inhibitors, wherein the inhibitor of the activity or expression of RFC40 is selected from the group consisting of a small interfering RNA (siRNA), microRNA (miRNA), an antisense polynucleotide, a ribozyme and a short-hairpin RNA (shRNA). In embodiments the inhibitor comprises or consists of a nucleic acid sequence complementary to, or engineered from, a naturally-occurring polynucleotide sequence. In embodiments, the nucleic acids can be approximately 17-30 contiguous nucleotides of a nucleic acid encoding RFC40 polypeptide, or the reverse complement of a nucleic acid encoding RFC40.

The method includes in certain embodiments use of an inhibitor, wherein the inhibitor inhibits the activity and/or expression of RFC40 and comprises a nucleic acid sequence complementary to, or engineered from, a naturally-occurring polynucleotide sequence of about 17 to about 30 contiguous nucleotides of the RFC40 nucleic acid of FIG. 18 (SEQ ID NO:2).

In a particular aspect the inhibitor is selected from a cAMP modulator, an inhibitor of CDK/cyclin E complexes, a protein kinase A (PKA) inhibitor, and an antibody against RFC40. In embodiments, the inhibitor is an indole-3 carbinole compound, olomoucine or roscovitine or 8-Cl-cAMP.

Since RFC40 has been shown to interact with RIα of protein kinase A, and this interaction facilitates or is required for nuclear translocation and activity thereby of RFC40, the inhibitor may be a compound or agent that blocks nuclear translocation of RFC40 and/or interaction of RFC40 with RIα of protein kinase A.

The invention includes a pharmaceutical composition(s) comprising a modulator, particularly an inhibitor of RFC40 for use in prophylaxis and/or therapy of cancer, particularly breast cancer. Such pharmaceutical composition(s) may comprise an agent selected from the group consisting of a small interfering RNA (siRNA), microRNA (miRNA), an antisense polynucleotide, a ribozyme and a short-hairpin RNA (shRNA), wherein said agent comprises a nucleic acid sequence complementary to, or engineered from, a naturally-occurring polynucleotide sequence of about 17 to about 30 contiguous nucleotides of a nucleic acid sequence encoding RFC40, and combinations thereof, and may further comprise a pharmaceutically acceptable carrier, vehicle or diluent.

In embodiments, the invention includes a pharmaceutical composition(s) comprising an agent which inhibits the expression, nuclear translocation, RIα interaction, or activity of RFC40, and a pharmaceutically acceptable carrier for use in the treatment of breast cancer.

In an embodiment, the disclosure includes a pharmaceutical composition for use in prophylaxis and/or therapy of cancer, the composition comprising a pharmaceutically acceptable carrier and a polynucleotide, wherein the polynucleotide comprises a sequence selected from SEQ ID NO:3 (CUUGUAAUGCUUCGGAUAA—RFC40-siRNA-S1); SEQ ID NO:4 (GAACUGCCGUGGGUUGAAA—RFC40-siRNA-S2); SEQ ID NO:5 (CGGCAAGACCACAAG-CAUU—RFC40-siRNA-S3); SEQ ID NO:6 (GCUGUG-CAGUCCUCCGGUA—RFC40-siRNA-S4); SEQ ID NO:7 (ACAGGUGAGGUUCUUGGGAGCC—miR-hsa-125a-3p); SEQ ID NO:8 (aCAGGUGAUCCACUUGggagcc—modified miR#1); SEQ ID NO:9 (aCAGGUGAGGAUAA-CAggagcc—modified miR#2) and combinations thereof. In embodiments an shRNA can be used. In an embodiment the shRNA comprises or consists of the sequence ACUAC-GAACUGCCGUGGGUUGAAAAAUAU (SEQ ID NO:15) or GUCCCGCUGUGCAGUCCUCCGGUACACAA (SEQ ID NO:16). As is well known in the art, shRNA can be introduced into target cells using any suitable compositions and methods. In an embodiment, the shRNA is introduced to the cell by way of a lentiviral expression system. Suitable lentiviral expression systems are known and are commercially available and can be adapted to express shRNA sequences and/or siRNA sequences disclosed herein.

In embodiments, the pharmaceutical composition comprises one or more polynucleotides which comprise or consist of SEQ ID NO:7, SEQ ID NO:8 or SEQ ID NO:9. In embodiments, the pharmaceutical formulation is provided in a sealed container in an article of manufacture, wherein the article of manufacture comprises packaging and printed material, wherein the printed material provides an indication that the pharmaceutical composition is for prophylaxis and/or therapy of cancer, such as breast cancer. The printed information can be provided on a label, or on a paper insert, or printed on the packaging material itself. The printed information can include information that identifies the pharmaceutical agents (i.e., polynucleotides targeted to RFC40) in the package, and instructions for taking or administering the pharmaceutical composition. In embodiments, the polynucleotides are provided in a pharmaceutical formulation in one or more closed or sealed vials, bottles, or any other suitable packaging for the sale, or distribution, or use of pharmaceutical compositions which comprise polynucleotides for use in prophylaxis and/or therapy of cancer. In embodiments, polynucleotides are provided in a form suitable for reconstitution into a liquid pharmaceutical composition with suitable concentrations of the polynucleotides. In embodiments, the indication provided by the printed material is an indication that the pharmaceutical composition is for prophylaxis and/or therapy of estrogen positive, or estrogen negative, or progesterone/estrogen/HER2 negative breast cancer.

In another aspect, a method is provided for prophylaxis and or therapy of cancer, including breast cancer, in a mammal comprising administering to said mammal the above composition(s). The method may further comprise administering an anticancer agent selected from an anti-mitotic agent, an immunomodulatory agent, and an agent targeting growth factor or estrogen receptors.

In an embodiment, the disclosure includes a method for inhibiting growth of cancer cells. The method comprises introducing into cancer cells at least one polynucleotide, wherein the polynucleotide comprises a sequence selected from SEQ ID NO:3, SEQ ID NO:4, SEQ ID NO:5, SEQ ID NO:6, SEQ ID NO:7, SEQ ID NO:8, or SEQ ID NO:9, and wherein subsequent to the introducing growth of the cancer cells is inhibited. In embodiments, the cancer cells are breast cancer cells. In certain aspects, the cancer cells are estrogen positive, estrogen negative or progesterone/estrogen/HER2 negative breast cancer cells (triple-negative breast cancer cells).

The diagnostic utility of the present invention includes in certain embodiments determining RFC40 protein amounts and/or gene amplification and/or expression in diagnosis and prognosis of cancer, particularly breast cancer. The disclosure provides in various embodiments methods for determining or prognosing/prognosticating breast cancer in an individual comprising assessing of levels or activity of RFC40 protein, RFC40 mRNA or RFC40 gene amplification in breast tissue, whereby an individual having breast cancer or malignancy has elevated levels or activity of RFC40 protein, RFC40 mRNA or RFC40 gene amplification versus a normal or benign control. In one embodiment, the disclosure includes a method for aiding in diagnosis of breast cancer in an individual. The method comprises testing a sample comprising breast tissue cells obtained from the individual to determine an amount of RFC40 protein and/or RFC40 mRNA in the sample, whereby determining increased RFC40 protein and/or RFC40 mRNA relative to a non-cancer control aids in the diagnosis of breast cancer in the individual, and wherein determining an amount of RFC40 protein and/or RFC40 mRNA that is the same as the non-cancer control indicates the individual does not have breast cancer. In embodiments, testing the sample comprises amplification of the RFC40 mRNA from the sample using a polymerase chain reaction (PCR). In embodiments, the PCR is performed using a first primer comprising the sequence ATGGAGGTGGAGGCCGTCTGTG (SEQ ID NO:10) and second primer comprising the sequence CCTCTAGCCTGCTCACGGTGTCTTC (SEQ ID NO:11). In embodiments, the PCR amplification is quantitative real time PCR (qRT-PCR). In embodiments, the disclosure includes fixing the determining of RFC40 mRNA and/or protein in a tangible medium of expression. In embodiments, the tangible medium of expression is transmitted or transported to a health care provider in order to aid in a diagnosis. In other embodiments, the disclosure includes determining an increased copy number of the RFC40 gene relative to a normal, non-cancer control. In embodiments, copy number can be determined using FISH-based approaches. In embodiments, determining an increase in RFC40 mRNA and/or protein is considered indicative of the presence of an increased copy number of the RFC40 gene in cancer cells from which the increased mRNA and/or protein was determined.

In certain approaches, after determining an increased RFC40 protein and/or mRNA relative to a non-cancer control, the method further comprising testing the sample to determine whether the breast tissue cells are estrogen positive, estrogen negative or progesterone/estrogen/HER2 negative breast cancer cells. In embodiments, the disclosure includes determining an increased RFC40 protein and/or mRNA relative to the non-cancer control and subsequently administering to the individual a pharmaceutical composition as described herein.

In certain embodiments, the disclosure includes RFC40 modulation, particularly inhibition, in assays to screen for specific cancer agents, particularly agents that alter cell growth, proliferation, division or progression from G1 to S phase particularly in malignant or cancerous cells versus normal or benign cells, which is a hallmark and useful capability for anti-cancer compounds and agents.

Thus, another aspect of the invention provides a method for identifying a compound that inhibits growth and/or cell division in breast cancer cells, said method comprising:
a) contacting a test compound with an RFC40 polypeptide, fragments or functional derivatives thereof or with a nucleic acid encoding RFC40 or a functional derivative thereof;
b) measuring the expression or an activity of RFC40 polypeptide; and
c) identifying a compound capable of inhibiting the expression or activity of said polypeptide whereby inhibition of expression or activity of said polypeptide results in or is associated with inhibition of growth and/or cell division in breast cancer cells.

Another aspect provides a method for identifying a compound that inhibits growth and/or cell division in breast cancer cells, said method comprising:
a) contacting a test compound with an RFC40 polypeptide, fragments or functional derivatives thereof or with a nucleic acid encoding RFC40 or a functional derivative thereof;
b) measuring the expression or an activity of said polypeptide and identifying and/or measuring inhibition or reduction of the expression or an activity of said polypeptide by the test compound;
c) contacting the test compound with a population of breast cancer cells;
d) measuring a property related to or indicating growth or cell division of said cells or determining the number of said cells; and
e) identifying a compound capable of inhibiting growth and/or cell division in breast cancer cells and demonstrating inhibition or reduction of the expression or an activity of said polypeptide or nucleic acid.

The above methods for identifying compounds may additionally comprise the step of comparing the compound to be tested to a control. The RFC40 polypeptide in the methods may be coupled to a detectable label. The polypeptide sequence in steps (a) and (b) may be performed utilizing an in vitro cell-free preparation or may be performed in a cell or cells particularly in mammary cells or in breast cancer cells, including cell lines or primary cells.

The invention includes an assay system for screening of potential drugs effective to modulate cell division and/or proliferation of target cancer cells, particularly breast cancer cells, by inhibiting RFC40 expression or activity in the target cells. In one instance, the test drug could be administered to a cellular sample with a cell proliferation agent or to breast cancer cells, to determine its effect on expression or activity of RFC40 in the presence of the test drug, by comparison with a control normal or benign cell or a control in the absence of a test drug.

In an assay, a control quantity of RFC40 or antibodies thereto, or the like may be prepared and labeled with an enzyme, a specific binding partner and/or a radioactive element, and may then be introduced into a cellular sample. In the instance where a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence or activity of RFC40 protein or mRNA, or to identify drugs or other agents that may mimic or block their activity. The system or test kit may comprise a labeled component prepared by one of the radioactive and/or enzymatic techniques discussed herein, coupling a label to the RFC40, their agonists and/or antagonists, and one or more additional immunochemical reagents, at least one of which is a free or immobilized ligand, capable either of binding with the labeled component, its binding partner, one of the components to be determined or their binding partner(s).

In another aspect the disclosure includes a kit, such as an article of manufacture, for use aiding in diagnosis of cancer in an individual. The kit can comprise packaging and at least one sealed container which contains a first primer comprising the sequence ATGGAGGTGGAGGCCGTCTGTG (SEQ ID NO:10) and second primer comprising the sequence CCTCTAGCCTGCTCACGGTGTCTTC (SEQ ID NO:11), the packaging further comprising printed material, the printed material providing an indication that the first and second primers are for use in polymerase chain reaction amplification of RFC40 mRNA into a cDNA, wherein the amount of RFC40 mRNA is diagnostic of the presence or absence of the cancer. The printed material that is part of the kit can provide an indication that the amount of RFC40 mRNA is diagnostic of the presence or absence of breast cancer. The kit can also include at least one additional container, the additional container comprising at least one buffer for use in polymerase chain reaction amplification of the RFC40 mRNA.

Other objects and advantages will become apparent to those skilled in the art from a review of the following description which proceeds with reference to the following illustrative drawings.

BRIEF DESCRIPTION OF THE DRAWINGS

FIGS. 1A and 1B (A) is a schematic representation of overexpression of RFC40 protein and of RFC40 message in breast cancers, including in estrogen positive and estrogen negative and progesterone/estrogen/HER2 negative breast cancers; (B) provides the amino acid sequence of human RFC40 (RFC2) (Accession/UniProtKB/Swiss-Prot: P35250.3) (SEQ ID NO:1).

FIGS. 2A and 2B Western blot analyses of RFC40 using MCF10A (A and B), MCF7 (A) MDA-MB-231 (A) and MDA-MB-468 (B) cell lysates. β-Actin was used as loading control. Each well contains 35 µg of total protein lysate.

FIG. 4 (A) A 96 cores patient BTMAs containing 12 normal and 36 breast cancer samples in duplicates were subjected to immunohistochemical analyses using polyclonal anti-RFC40 followed by incubation with HRP-conjugated secondary antibodies for 1 h. Images of the stained sections were collected using Dako Cytomation system. (B) Graph represents the RFC40 staining scores (intensity of staining× percentage of cells stained) in normal, estrogen positive (ER+ ve) and estrogen negative (ER−ve) samples. Values are mean±SE. * indicates P<0.05 vs. Normal.

FIG. 8 96 cores patient BTMAs containing 12 normal and 36 breast cancer samples in duplicates were subjected to immunohistochemical analyses using polyclonal anti-RFC40 followed by incubation with HRP-conjugated secondary antibodies for 1 h. Images of the stained sections were collected using Dako Cytomation system. The number of normal/benign and cancer cells with RFC40 positive nuclear staining (arrows) was measured for 3 fields/sample.

FIG. 18 provides human RFC40 mRNA nucleic acid sequence (SEQ ID NO:2) and the Smartpool siRNA RNA sequences for each of RFC40-siRNA-S1 (SEQ ID NO:3), RFC40-siRNA-S2 (SEQ ID NO:4), RFC40-siRNA-S3 (SEQ ID NO:5), and RFC40-siRNA-S4 (SEQ ID NO:6). The non-targeting siRNA sequence (NT) (SEQ ID NO:14) is also indicated. The RFC40 mRNA sequence is provided as the cDNA sequence.

FIG. 21A-21B MCF10A and MDA-MBA-468 cells were transfected with Smartpool RFC40-SiRNA (100 nM) for 72 hr. Cells were incubated with Hoechst 33342 for 45 min at 37° C. Immunofluorescent microscopy was performed to determine the presence of apoptotic nuclei in the RFC40-siRNA treated MCF10A and MDA-MB-468 cells, respectively, using Nikon microscope (20× magnification). Unt=untransfected, NT=non-targeting.

FIGS. 22A and 22B MCF10A (non-cancerous; A) and MDA-MB-231 (estrogen negative breast cancer cells; B) cells were transfected with non targeting (NT) and RFC40-S1/S2/S3/S4-siRNA (100 nM; four individual sequences) for 72 hr. Cells lysates were subjected to Western blot analysis using anti-RFC40 antibody. β-Actin was used as loading control.

FIGS. 23A and 23B MCF10A and MDA-MB-231 cells were transfected with RFC40-SiRNA-S1/S2/S3/S4 (100 nM) for 72 hr. Cell number analses was performed using Cyquant cell number analyses kit. Graphs represent the number of MCF10A (A; n=8) and MDA-MB-231 (B; n=8) cells vs the untransfected (UT) and RFC40-siRNA-S1/S2/S3/S4 treated cells.

FIG. 24 depicts miR-hsa-125-3p miRNA sequence and two modified designed alternative miR sequences (#1 and #2; shown in red) aligned with RFC40 RNA sequence. The miR-hsa-125-3p miRNA sequence is SEQ ID NO:7. The #1 modified sequence is SEQ ID NO:8. The #2 modified sequence is SEQ ID NO:9. The RFC2-mRNA-3'UTR alignment sequence shown in the 5'→3' direction is SEQ ID NO:17 ( ccgaggCAGGUGGAUCACCUGa).

FIGS. 25A and 25B MCF10A (A) and MDA-MB-231 (B) cells were transfected with negative control miRNA31 and miR-hsa-125a-3p (100 nM), respectively for 72 hr. Cells lysates were subjected to Western blot analysis using anti-RFC40 antibody. β-Acin was used as loading control.

FIGS. 26A and 26B MCF10A and MDA-MB-231cells were transfected with miR-hsa-125a-3p (100 nM) for 72 hr. The cells were trypsinized, resuspended in 1×PBS and counted using a hemocytometer. Graph represents the number of MCF10A (A; n=10) and MDA-MB-231 (B; n=9) cells vs the untransfected (UT) and miR-hsa-125a-3p treated cells.

DETAILED DESCRIPTION

Figure 3:
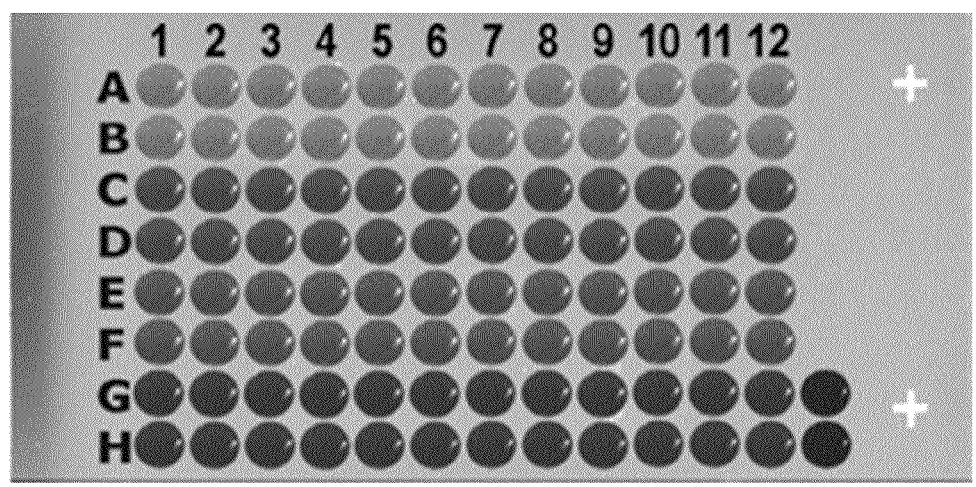
FIG. 3 Schematic representation of 96 cores patient breast cancer tissue arrays (BTMAs) containing 12 normal, reactive and benign tumors of the breast (pink) and 36 breast cancer samples (purple/blue) in duplicates.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "RFC40, "RFC2", "Replication Factor C 40" and "Replication Factor C 40 kD protein" and any variants not specifically listed, may be used herein interchangeably, and as used throughout the present application and claims refer to proteinaceous material including single or multiple proteins, and extends to those proteins having the amino acid sequence data described herein and presented in FIG. 1 (SEQ ID NO:1) and the encoding nucleic acid sequence in FIG. 18 (SEQ ID NO:2), and the profile of activities set forth herein and in the Claims. Accordingly, proteins displaying substantially equivalent or altered activity are likewise contemplated.

These modifications may be deliberate, for example, such as modifications obtained through site-directed mutagenesis, or may be accidental, such as those obtained through mutations in hosts that are producers of the complex or its named subunits. Also, the terms "RFC40, "RFC2", "Replication Factor C 40" and "Replication Factor C 40 kD protein" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | AMINO |
| 1-Letter | 3-Letter | ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

Primers are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding RFC40 which code for a polypeptide having the same amino acid sequence as provided in FIG. 1 (SEQ ID NO:1), but which are degenerate to the sequence of FIG. 18 (SEQ ID NO:2). By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCC or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |

-continued

| | |
|---|---|
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in RFC40 sequence as set out in FIG. 18 (SEQ ID NO:2) such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino acids with nonpolar R groups: Alanine, Valine, Leucine, Isoleucine, Proline, Phenylalanine, Tryptophan, Methionine Amino acids with uncharged polar R groups: Glycine, Serine, Threonine, Cysteine, Tyrosine, Asparagine, Glutamine Amino acids with charged polar R groups (negatively charged at Ph 6.0): Aspartic acid, Glutamic acid Basic amino acids (positively charged at pH 6.0): Lysine, Arginine, Histidine (at pH 6.0)

Another grouping may be those amino acids with phenyl groups: Phenylalanine, Tryptophan, Tyrosine Another grouping may be according to molecular weight (i.e., size of R groups):

| | |
|---|---|
| Glycine | 75 |
| Alanine | 89 |
| Serine | 105 |
| Proline | 115 |
| Valine | 117 |
| Threonine | 119 |
| Cysteine | 121 |
| Leucine | 131 |
| Isoleucine | 131 |
| Asparagine | 132 |
| Aspartic acid | 133 |
| Glutamine | 146 |
| Lysine | 146 |
| Glutamic acid | 147 |
| Methionine | 149 |
| Histidine (at pH 6.0) | 155 |
| Phenylalanine | 165 |
| Arginine | 174 |

-continued

| | |
|---|---|
| Tyrosine | 181 |
| Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free NH$_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces □-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The phrase "pharmaceutically acceptable" refers to molecular entities and compositions that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20$^N$C below the predicted or determined T$_m$ with washes of higher stringency, if desired.

In one aspect, the present invention identifies and validates a DNA replication protein, RFC40, as a non-receptor based molecular marker and specific target for breast cancer, irrespective or its receptor status, including TNBC. The studies provided herein establish that RFC40 protein and message, as well as RFC40 gene copy numbers, are increased in breast cancers, including in estrogen sensitive, estrogen resistant and triple negative breast cancer (TNBC). The present studies demonstrate that inhibition or modulation of RFC40 such that its activity or expression is reduced or blocked results in reduction in cell numbers and inhibition of cell proliferation or division in estrogen positive (ER positive), estrogen negative (ER negative), and progesterone, estrogen and human epidermal growth factor receptor 2-HER2 negative or triple negative breast cancer (TNBC) cells.

Thus, RFC40 provides a non-receptor diagnostic and prognostic marker and a therapeutic or interventional target involved in cell division and proliferation which is independent of growth factor and endocrine receptor status. Inhibition or modulation of RFC40 is therefore applicable in early stage breast cancer, late stage breast cancer, on drug failure or resistance to receptor-based therapies, and in instances of recurrence.

Further, the studies herein establish that RFC40 can be specifically inhibited in cancer cells, without effects in concomitant normal or benign cells, thereby providing RFC40 as a specific anti-cancer agent with onco-specificity in rapidly dividing and proliferating cancer cells, without toxic or unintended effects in normal cells.

The possibilities both diagnostic and therapeutic that are raised in part by the recognition of RFC40 gene amplification and increased message and protein in cancer cells, particularly in breast cancer cells and irrespective of growth factor or estrogen receptor status. The present invention contemplates pharmaceutical intervention in the expression, activity or necessary protein interactions of RFC40 in a cancer cell, to modulate the cell division and proliferation, including particularly the G1 to S phase transition.

Thus, in instances where it is desired to reduce or inhibit cancer, including but not necessarily limited to breast cancer, cell division or proliferation, agents or compounds may be introduced to block RFC40-mediated function or activity in a cancer cell, including the expression of RFC40, the activity of RFC40 protein, or the interaction of RFC40 with those factors causally connected with its activity or necessary nuclear localization.

RFC40 inhibitors or agents modulating RFC40-mediated cellular effects may be prepared in pharmaceutical compositions, with a suitable carrier and at a strength effective for administration by various means to a patient experiencing an adverse medical condition associated with specific enhanced expression or activity of RFC40, or in hyper-proliferative diseases, such as cancer, including breast cancer, for the treatment thereof. A variety of administrative techniques may be utilized, among them parental techniques such as subcutaneous, intravenous and intra-peritoneal injections, catheterizations and the like, oral administration, and dermal applications. Average quantities of the RFC40 inhibitors or agents may vary and in particular should be based upon the recommendations and prescription of a qualified physician or veterinarian.

Also, antibodies directed against RFC40, including both polyclonal and monoclonal antibodies, and drugs that modulate the production or activity of RFC40 or that bind with affinity to RFC40 protein, message or nucleic acid, and/or their subunits may possess certain diagnostic applications and may for example, be utilized for the purpose of detecting and/or measuring conditions such as cancer, including breast cancer.

Methods for producing polyclonal anti-polypeptide antibodies are well-known in the art. A monoclonal antibody, typically containing Fab and/or F(ab')$_2$ portions of useful antibody molecules, can be prepared using the hybridoma technology described in *Antibodies—A Laboratory Manual*, Harlow and Lane, eds., Cold Spring Harbor Laboratory, New York (1988), which is incorporated herein by reference. The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against RFC40 peptides can be screened for various properties; i.e., isotype, epitope, affinity, etc. Of particular interest are monoclonal antibodies that neutralize the activity of the RFC40 or its subunits. Such monoclonals can be readily identified in RFC40 activity assays.

Preferably, the anti-RFC40 antibody used in the diagnostic methods of this invention is an affinity purified polyclonal antibody. More preferably, the antibody is a monoclonal antibody (mAb). In addition, it is preferable for the anti-RFC40 antibody molecules used herein be in the form of Fab, Fab', F(ab')$_2$ or F(v) portions of whole antibody molecules.

As suggested earlier, the diagnostic method of the present invention comprises examining a cellular sample or medium by means of an assay including an effective amount of an antagonist to a ~/protein, such as an anti-~ antibody, preferably an affinity-purified polyclonal antibody, and more preferably a mAb. In addition, it is preferable for the anti-~ antibody molecules used herein be in the form of Fab, Fab', F(ab')$_2$ or F(v) portions or whole antibody molecules. As previously discussed, patients capable of benefiting from this method include those suffering from cancer, a pre-cancerous lesion, a viral infection or other like pathological derangement. Methods for isolating the ~ and inducing anti-~ antibodies and for determining and optimizing the ability of anti-~ antibodies to assist in the examination of the target cells are all well-known in the art.

The present invention further contemplates pharmaceutical and therapeutic compositions useful in practicing the therapeutic methods of this invention. A subject pharmaceutical or therapeutic composition includes, in admixture, a pharmaceutically acceptable excipient (carrier) and one or more of an RFC40 inhibitory agent or compound as described herein as an active ingredient.

The preparation of therapeutic compositions which contain nucleic acids polypeptides, analogs or active fragments, chemical agents, organic or inorganic compounds, etc as active ingredients is well understood in the art. Such compositions may be prepared as injectables, either as liquid solutions or suspensions. Solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A nucleic acid, polypeptide, analog or active fragment or other compound or agent can be formulated into the pharmaceutical or therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic RFC40 inhibitory agent or compound containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's cellular or immune system to utilize the active ingredient, and degree of inhibition of RFC40 activity or expression or of cell division or proliferation desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and subsequent administration are also variable, but are typified by an initial administration followed by repeated doses at one or more hour, day, week or month intervals by a subsequent administration. Alternatively, continuous (e.g. intravenous) infusion sufficient to maintain appropriate and sufficient concentrations in the blood or at the cancer site cellular environment are contemplated.

The pharmaceutical or therapeutic compositions may further include an effective amount of the RFC40 inhibitory agent or compound, and one or more of the following active ingredients: an anti-mitotic, an immune-omodulator, a growth factor modulator, an interleukin or interferon, a kinase inhibitor, an anti-cancer antibody such as a HER2 antibody and/or an EGFR antibody, an antibiotic, a steroid.

As used herein, "pg" means picogram, "ng" means nanogram, "ug" or "µg" mean microgram, "mg" means milligram, "ul" or "µl" mean microliter, "ml" means milliliter, "l" means liter.

Another feature of this invention is the expression of the nucleic acid sequences including DNA and RNA sequences disclosed herein, including in particular the RFC40 inhibitory agents or compounds. As is well known in the art, nucleic acid sequences may be expressed by operatively linking them to an expression control sequence in an appropriate expression vector and employing that expression vector to transform an appropriate unicellular host. Such operative linking of a nucleic acid sequence of this invention to an expression control sequence, of course, includes, if not already part of the DNA or RNA sequence, the provision of an initiation codon, ATG, in the correct reading frame upstream of the DNA or RNA sequence.

A wide variety of host/expression vector combinations may be employed in expressing the nucleic sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col El, pCR1, pBR322, pMB9 and their derivatives, plasmids such as RP4; phage DNAS, e.g., the numerous derivatives of phage λ, e.g., NM989, and other phage DNA, e.g., M13 and filamentous single stranded phage DNA; yeast plasmids such as the 2µ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a nucleic acid sequence operatively linked to it—may be used in these vectors to express the nucleic acid sequences of this invention. Such expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast ∀-mating factors, and other sequences known to control the expression of genes of prokaryotic or eukaryotic cells or their viruses, and various combinations thereof.

A wide variety of unicellular host cells are also useful in expressing the nucleic acid sequences of this invention. These hosts may include well known eukaryotic and prokaryotic hosts, such as strains of E. coli, Pseudomonas, Bacillus, Streptomyces, fungi such as yeasts, and animal cells, such as CHO, Rl.l, B-W and L-M cells, African Green Monkey kidney cells (e.g., COS 1, COS 7, BSC1, BSC40, and BMT10), insect cells (e.g., Sf9), and human cells and plant cells in tissue culture.

One skilled in the art will be able to select the proper vectors, expression control sequences, and hosts without undue experimentation to accomplish the desired expression without departing from the scope of this invention.

In an embodiment, a nucleic acid sequence provided or of use in accordance with the present invention can be prepared synthetically using methods known and available in the art, including commercially available synthesizers, laboratory bench methods and in vitro methods.

Synthetic nucleic acid sequences allow convenient construction of analogs or "muteins". Alternatively, nucleic acid having or encoding muteins can be made by site-directed mutagenesis of native genes or cDNAs, cloned or synthetic nucleic acid sequences and muteins can be made directly using conventional polypeptide or nucleic acid synthesis.

A general method for site-specific incorporation of unnatural amino acids into proteins is described in Christopher J. Noren, Spencer J. Anthony-Cahill, Michael C. Griffith, Peter G. Schultz, Science, 244:182-188 (April 1989). This method may be used to create analogs with unnatural amino acids.

Expression of RFC40 can be inhibited by various means including expression inhibitory agents which are nucleic acids or nucleic acid-based and that have binding activity for RFC40 nucleic acid and thereby exert an inhibitory effect on expression, translation and thereby reduce effective activity of RFC40 in cells, particularly in cancer cells, particularly breast cancer cells. Such an inhibitor of the activity or expression of RFC40 includes and may be a small interfering RNA (siRNA), microRNA (miRNA), an antisense polynucleotide, a ribozyme or a short-hairpin RNA (shRNA), particularly wherein said inhibitor comprises a nucleic acid sequence complementary to, or engineered from, a naturally-occurring polynucleotide sequence of about 17 to about 30 contiguous nucleotides of a nucleic acid encoding RFC40 polypeptide.

miRs MicroRNAs (miRNAs) are ubiquitous regulators of biological processes involved in normal development, in differentiation and in diseases, including cancer. They act by regulating gene expression at the transcriptional and translational levels (Bartel et al (2004) Cell 116:281-297). miRNAs were initially discovered by analysis of mutations causing developmental defects in *Caenorhabditis elegans* (Lee R. C. et al (1993) Cell, 75, 843-854) and altered miRNA expression has been further demonstrated in human cancer, including leukemia (Calin G. A. et al (2004) PNAS USA 101: 11755-11760; Hayashita Y et al (2005) Cancer Res 65:9628-9632; Johnson S. M. et al (2005) Cell 120:635-647; Lu J et al (2005) Nature 435:834-838; Venturini L et al (2007) Blood 109: 4399-4405). MicroRNAs (miRNA) regulate gene expression in a sequence specific manner by hybridization and recruitment of multi-protein complexes to complementary messenger RNA (mRNA) target sequences. miRNA function can transiently be antagonized by antagomirs—chemically modified oligonucleotides complementary to individual miRNAs.

A single miRNA can target hundreds of messenger RNAs and thereby modulate protein output from their respective genes (Bartel D P (2009) Cell 136:215-233). Therefore a single or specific set of miRNAs may control discrete physiological processes by regulating the production of a few proteins that coordinate single or interrelated cellular events (e.g., cell proliferation) (Baltimore D et al (2008) Nat Immunol 9:839-845; Bartel D P (2009) Cell 136:215-233).

Numerous miRNAs are known and have been identified. Known miRNAs are accessible by name with sequence information and characteristics via public database(s) including the miRBase database, mirbase.org; Griffiths-Jones S (2003) Methods Mol Biol 342:129-138. Nonetheless, their specific roles in initiation and/or progression of disease(s) and their particular value as targets for therapies or as modulators of disease, including specific cancer(s) are, in many instances, still being defined. Specific inhibition of one or more miRNAs can be achieved using antagonists or antagomirs, which comprise complementary sequences, including oligonucleotides and nucleic acids, which specifically inhibit or block the expression and activity of miRNA(s). Antagomirs of miRNA(s) are provided and assessed herein, with demonstrated anti-oncogenic and anti-proliferative activity.

siRNAs. A particular inhibitory agent is a small interfering RNA (siRNA, particularly small hairpin RNA, "shRNA"). siRNA, particularly shRNA, mediate the post-transcriptional process of gene silencing by double stranded RNA (dsRNA) that is homologous in sequence to the silenced RNA. siRNA according to the present invention comprises a sense strand of 15-30, particularly 17-30, most particularly 17-25 nucleotides complementary or homologous to a contiguous 17-25 nucleotide sequence selected from the group of exemplary siRNA sequences described in FIG. 18, and an antisense strand of 15-30, particularly 17-30, most particularly 17-25, more specifically 19-21 nucleotides complementary to the sense strand of encoding RNA, particularly complementary to encoding nucleic acid as set out in FIG. 18. In certain embodiments, siRNA comprises sense and anti-sense strands that are 100 percent complementary to each other and the TARGET polynucleotide sequence. In embodiments the siRNA further comprises a loop region linking the sense and the antisense strand.

A self-complementing single stranded shRNA molecule polynucleotide according to the present invention comprises a sense portion and an antisense portion connected by a loop region linker. Particularly, the loop region sequence is 4-30 nucleotides long, more particularly 5-15 nucleotides long and most particularly 8 or 12 nucleotides long. Self-complementary single stranded siRNAs form hairpin loops and are more stable than ordinary dsRNA. In addition, they are more easily produced from vectors.

Analogous to antisense RNA, the siRNA can be modified to confirm resistance to nucleolytic degradation, or to enhance activity, or to enhance cellular distribution, or to enhance cellular uptake, such modifications may consist of modified internucleoside linkages, modified nucleic acid bases, modified sugars and/or chemical linkage the siRNA to one or more moieties or conjugates. The nucleotide sequences are selected according to siRNA designing rules that give an improved reduction of the TARGET sequences compared to nucleotide sequences that do not comply with these siRNA designing rules (For a discussion of these rules and examples of the preparation of siRNA, WO 2004/094636 and US 2003/0198627, are hereby incorporated by reference).

The present invention extends to antisense oligonucleotides and ribozymes that may be used to interfere with the expression of the RFC40 at the translational level. This approach utilizes antisense nucleic acid and ribozymes to block translation of a specific mRNA, either by masking that mRNA with an antisense nucleic acid or cleaving it with a ribozyme. Antisense nucleic acids are DNA or RNA molecules that are complementary to at least a portion of a specific mRNA molecule. (See Weintraub, 1990; Marcus-Sekura, 1988.) In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into RFC40-producing cells. Antisense methods have been used to inhibit the expression of many genes in vitro (Marcus-Sekura, 1988; Hambor et al., 1988).

Ribozymes are RNA molecules possessing the ability to specifically cleave other single stranded RNA molecules in a manner somewhat analogous to DNA restriction endonucleases. Because they are sequence-specific, only mRNAs with particular sequences are inactivated. Ribozymes are catalytic RNA molecules (RNA enzymes) that have separate catalytic and substrate binding domains. The substrate binding sequence combines by nucleotide complementarity and, possibly, non-hydrogen bond interactions with its target sequence. The catalytic portion cleaves the target RNA at a specific site. The substrate domain of a ribozyme can be engineered to direct it to a specified mRNA sequence. The ribozyme recognizes and then binds a target mRNA through complementary base pairing. Once it is bound to the correct target site, the ribozyme acts enzymatically to cut the target mRNA. Cleavage of the mRNA by a ribozyme destroys its ability to direct synthesis of the corresponding polypeptide. Once the ribozyme has cleaved its target sequence, it is released and can repeatedly bind and cleave at other mRNAs.

Exemplary ribozyme forms include a hammerhead motif, a hairpin motif, a hepatitis delta virus, group I intron or RNaseP RNA (in association with an RNA guide sequence) motif or *Neurospora* VS RNA motif. Ribozymes possessing a hammerhead or hairpin structure are readily prepared since these catalytic RNA molecules can be expressed within cells from eukaryotic promoters (Chen, et al. (1992) Nucleic Acids Res. 20:4581-9). A ribozyme of the present invention can be expressed in eukaryotic cells from the appropriate DNA vector. If desired, the activity of the ribozyme may be augmented by its release from the primary transcript by a second ribozyme (Ventura, et al. (1993) Nucleic Acids Res. 21:3249-55).

Ribozymes may be chemically synthesized by combining an oligodeoxyribonucleotide with a ribozyme catalytic domain (20 nucleotides) flanked by sequences that hybridize to the TARGET mRNA after transcription. The oligodeoxyribonucleotide is amplified by using the substrate binding sequences as primers. The amplification product is cloned into a eukaryotic expression vector.

Ribozymes are expressed from transcription units inserted into DNA, RNA, or viral vectors. Transcription of the ribozyme sequences are driven from a promoter for eukaryotic RNA polymerase I (pol (I), RNA polymerase II (pol II), or RNA polymerase III (pol III). Transcripts from pol II or pol III promoters will be expressed at high levels in all cells; the levels of a given pol II promoter in a given cell type will depend on nearby gene regulatory sequences. Prokaryotic RNA polymerase promoters are also used, providing that the prokaryotic RNA polymerase enzyme is expressed in the appropriate cells (Gao and Huang, (1993) Nucleic Acids Res. 21:2867-72). It has been demonstrated that ribozymes expressed from these promoters can function in mammalian cells (Kashani-Sabet, et al. (1992) Antisense Res. Dev. 2:3-15).

The antisense nucleic acids, siRNAs and miRs are particularly oligonucleotides and may consist entirely of ribonucleotides, modified ribonucleotides, deoxyribo-nucleotides, modified deoxyribonucleotides, or some combination of both. The nucleic acids can be synthetic oligonucleotides. The nucleic acids and oligonucleotides may be chemically modified, if desired, to improve stability and/or selectivity. Specific examples of some particular oligonucleotides envisioned for this invention include those containing modified backbones, for example, phosphorothioates, phosphotriesters, methyl phosphonates, short chain alkyl or cycloalkyl intersugar linkages or short chain heteroatomic or heterocyclic intersugar linkages. Since oligonucleotides are susceptible to degradation by intracellular nucleases, the modifications can include, for example, the use of a sulfur group to replace the free oxygen of the phosphodiester bond. This modification is called a phosphorothioate linkage. Phosphorothioate antisense oligonucleotides are water soluble, polyanionic, and resistant to endogenous nucleases. In addition, when a phosphorothioate antisense oligonucleotide hybridizes to its target (for example RFC40) site, the RNA-DNA duplex activates the endogenous enzyme ribonuclease (RNase) H, which cleaves the mRNA component of the hybrid molecule. Oligonucleotides may also contain one or more substituted sugar moieties. Particular oligonucleotides comprise one of the following at the 2' position: OH, SH, SCH3, F, OCN, heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. Similar modifications may also be made at other positions on the oligonucleotide, particularly the 3' position of the sugar on the 3' terminal nucleotide and the 5' position of 5' terminal nucleotide.

In addition, antisense oligonucleotides with phosphoramidite and polyamide (peptide) linkages can be synthesized. These molecules should be very resistant to nuclease degradation. Furthermore, chemical groups can be added to the 2' carbon of the sugar moiety and the 5 carbon (C-5) of pyrimidines to enhance stability and facilitate the binding of the antisense oligonucleotide to its TARGET site. Modifications may include 2'-deoxy, O-pentoxy, O-propoxy, O-methoxy, fluoro, methoxyethoxy phosphorothioates, modified bases, as well as other modifications known to those of skill in the art.

The DNA sequences described herein may thus be used to prepare antisense molecules against, and ribozymes that cleave mRNAs for RFC40 and their ligands.

Another aspect of the present invention relates to a method for identifying a compound that inhibits or reduces cell division or proliferation in cancer cells, particularly breast cancer. The method may comprise contacting mammalian cells with an expression-inhibiting agent that inhibits the translation in the cell of a polyribonucleotide encoding a RFC40 polypeptide. A particular embodiment relates to a composition comprising a polynucleotide including at least one antisense strand that functions to pair the agent with the target RFC40 mRNA, and thereby down-regulate or block the expression of target RFC40 polypeptide. The inhibitory agent particularly comprises antisense polynucleotide, a ribozyme, and a small interfering RNA (siRNA), wherein said agent comprises a nucleic acid sequence complementary to, or engineered from, a naturally-occurring polynucleotide sequence of RFC40, including as set out in FIG. 18 (SEQ ID NO:2).

One embodiment of the present invention relates to a method for identifying a compound that inhibits or reduces cell division or proliferation in cancer cells, particularly breast cancer, wherein the compound is an expression-inhibiting agent and is selected from the group consisting of antisense RNA, antisense oligodeoxynucleotide (ODN), a ribozyme that cleaves the polyribonucleotide coding for RFC40, a small interfering RNA (siRNA, particularly shRNA) that is sufficiently homologous to a portion of the polyribonucleotide coding for RFC40, including as set out in FIG. 18 (SEQ ID NO:2), such that the antisense RNA, ODN, ribozyme, particularly siRNA, particularly shRNA, interferes with the translation of the target RFC40 polyribonucleotide to the target RFC40 polypeptide.

Another embodiment of the present invention relates to a method for identifying a compound for treatment of cancer, particularly breast cancer, wherein said compound is an expression-inhibiting agent such as a nucleic acid expressing the antisense RNA, antisense oligodeoxynucleotide (ODN), a ribozyme that cleaves the polyribonucleotide coding for RFC40, including as set out in FIG. 18 (SEQ ID NO:2), a small interfering RNA (siRNA, particularly shRNA) that is sufficiently complementary to a portion of the polyribonucleotide coding for RFC40, including as set out in FIG. 18 (SEQ ID NO:2), such that the antisense RNA, ODN, ribozyme, particularly siRNA, particularly shRNA, interferes with the translation of the target RFC40 polyribonucleotide to the target RFC40 polypeptide. Particularly the expression-inhibiting agent is an antisense RNA, ribozyme, antisense oligodeoxynucleotide, or siRNA, particularly shRNA, comprising a polyribonucleotide sequence that complements at least about 17 to about 30 contiguous nucleotides of a nucleotide sequence coding for RFC40, including as set out in FIG. 18 (SEQ ID NO:2).

More particularly, the expression-inhibiting agent is an antisense RNA, ribozyme, antisense oligodeoxynucleotide, or siRNA, particularly shRNA, comprising a polyribonucleotide sequence that complements at least 15 to about 30, particularly at least 17 to about 30, most particularly at least 17 to about 25, more specifically at least 19 to about 21 contiguous nucleotides of a nucleotide sequence coding for RFC40, including as set out in FIG. 18 (SEQ ID NO:2). Particular embodiments thereof are provided herein, including as set out in FIG. 18 and in FIG. 24 and provided in miRNAS of miR-hsa-125a-3p (SEQ ID NO:7), modified miR#1 (SEQ ID NO:8), modified miR#2 (SEQ ID NO:9) and in siRNAs RFC40-siRNA-S1 (SEQ ID NO:3), RFC40-siRNA-S2 (SEQ ID NO:4), RFC40-siRNA-S3 (SEQ ID NO:5) and RFC40-siRNA-S4 (SEQ ID NO:6).

The down regulation of gene expression using antisense nucleic acids can be achieved at the translational or transcriptional level. Antisense nucleic acids of the invention are particularly nucleic acid fragments capable of specifically hybridizing with all or part of a nucleic acid encoding a target RFC40 polypeptide or the corresponding messenger RNA. In addition, antisense nucleic acids may be designed which decrease expression of the nucleic acid sequence capable of encoding a target RFC40 polypeptide by inhibiting splicing of its primary transcript. Any length of antisense sequence is suitable for practice of the invention so long as it is capable of down-regulating or blocking expression of a nucleic acid coding for target RFC40. Particularly, the antisense sequence is at least about 15-30, and particularly at least 17 nucleotides in length. The preparation and use of antisense nucleic acids, DNA encoding antisense RNAs and the use of oligo and genetic antisense is known in the art.

An aspect of these methods relates to the down-regulation or blocking of the expression of a target RFC40 polypeptide by the induced expression of a polynucleotide encoding an intracellular binding protein that is capable of selectively interacting with the target RFC40 polypeptide. An intracellular binding protein includes an activity-inhibitory agent and any protein capable of selectively interacting, or binding, with the polypeptide in the cell in which it is expressed and neutralizing the function of the polypeptide. Particularly, the intracellular binding protein may be an antibody, particularly a neutralizing antibody, or a fragment of an antibody or neutralizing antibody having binding affinity to an epitope of the RFC40 polypeptide, including as set out in FIG. 1 (SEQ ID NO:1). In embodiments, the intracellular binding protein is a single chain antibody.

Various embodiments of these methods comprises the expression-inhibitory agent selected from the group consisting of antisense RNA, antisense oligodeoxynucleotide (ODN), a ribozyme that cleaves the polyribonucleotide coding for RFC40, and a small interfering RNA (siRNA) that is sufficiently homologous to a portion of the RFC40 polyribonucleotide as set out in FIG. 18 (SEQ ID NO:2), such that the siRNA interferes with the translation of the target RFC40 polyribonucleotide to the target RFC40 polypeptide.

The present invention also relates to a variety of diagnostic applications, including methods for detecting the presence, amount or activity of RFC40 protein, messenger RNA or RFC40 gene amplification, by reference to the RFC40 proteins role in cancer and cancer cell proliferation and division, including in breast cancer. RFC40 antibodies are known and available in the art, including those utilized in the exemplary methods and assays provided herein and in the examples. Further RFC40 can be used to produce antibodies to itself by a variety of known techniques, and such antibodies could then be isolated and utilized as in tests for the presence of RFC40 in sample or cancer-suspecting cells.

The RFC40 in cells can be ascertained by the usual immunological procedures applicable to such determinations. A number of useful procedures are known, including as employed and utilized in the examples and studies described herein. Procedures which are useful may utilize either the RFC40 labeled with a detectable label, antibody $Ab_1$ labeled with a detectable label, or antibody $Ab_2$ labeled with a detectable label. The procedures may be summarized by the following equations wherein the asterisk indicates that the particle is labeled, and "~" stands for RFC40:

A. $\sim\!*+Ab_1=\sim\!*Ab_1$
B. $\sim\!+Ab^*=\sim\!Ab_1^*$
C. $\sim\!+Ab_1+Ab_2^*=\sim\!Ab_1Ab_2^*$ The procedures and their application are all familiar to those skilled in the art and accordingly may be utilized within the scope of the present invention. The "competitive" procedure, Procedure A, is described in U.S. Pat. Nos. 3,654,090 and 3,850,752. Procedure C, the "sandwich" procedure, is described in U.S. Pat. Nos. RE 31,006 and 4,016,043. Still other procedures are known such as the "double antibody," or "DASP" procedure. In each instance, the RFC40 forms complexes with one or more antibody(ies) or binding partners and one member of the complex is labeled with a detectable label. The fact that a complex has formed and, if desired, the amount thereof, can be determined by known methods applicable to the detection of labels. The labels most commonly employed for these studies are radioactive elements, enzymes, chemicals which fluoresce when exposed to ultraviolet light, and others.

A number of fluorescent materials are known and can be utilized as detectable labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. The RFC40 or its binding partner(s) can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluoro spectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. In embodiments the enzymes can be are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

In a further embodiment of this invention, commercial test kits suitable for use by a medical specialist may be prepared to determine the presence or amount of RFC40 activity, expression or RFC40 gene amplification in suspected cancer cells or biopsy or tumor samples. One class of such kits will contain at least the labeled RFC40 or its binding partner, for instance an antibody specific thereto, and directions, of course, depending upon the method selected, e.g., "competitive," "sandwich," "DASP" and the like. The kits may also contain peripheral reagents such as buffers, stabilizers, etc. In embodiments the kits comprise one or more PCR primers described herein.

Accordingly, a test kit may be prepared for the determination and quantitation of RFC40 protein in cells or a cellular or biopsy sample, comprising:

(a) a predetermined amount of at least one labeled immunochemically reactive component obtained by the direct or indirect attachment of the present RFC40 or a specific binding partner thereto, to a detectable label;

(b) other reagents; and (c) directions for use of said kit.

More specifically, the diagnostic test kit may comprise:

(a) a known amount of the RFC40 as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, and comprises:

(a) a labeled component which has been obtained by coupling the RFC40 to a detectable label;

(b) one or more additional immunochemical reagents of which at least one reagent is a ligand or an immobilized ligand, which ligand is selected from the group consisting of:

(i) a ligand capable of binding with the labeled component (a);

(ii) a ligand capable of binding with a binding partner of the labeled component (a);

(iii) a ligand capable of binding with at least one of the component(s) to be determined; and (iv) a ligand capable of binding with at least one of the binding partners of at least one of the component(s) to be determined; and (c) directions for the performance of a protocol for the detection and/or determination of one or more components of an immunochemical reaction between the RFC40 and a specific binding partner thereto.

In accordance with the above, an assay system for screening potential drugs effective to modulate the activity or expression of RFC40 may be prepared and is provided. The RFC40 may be introduced into a test system, and the prospective drug may also be introduced into the resulting cell culture, and the culture thereafter examined to observe any changes in the RFC40 activity of the cells, or in the proliferation or division of the cells, due either to the addition of the prospective drug alone, or due to the effect of added quantities of the known RFC40.

The invention may be better understood by reference to the following non-limiting Examples, which are provided as exemplary of the invention which are presented in order to more fully illustrate embodiments of the disclosure and should in no way be construed as limiting the scope of the invention.

Example 1

RFC40 is a Molecular Marker for Breast Cancer

Cancers with gene copy number amplification or chromosome polysomy usually are the most aggressive types, often associated and correlated with invasion, metastasis and recurrence, and cannot be corrected at the chromosomal level (Mizutani T et al (1993) Cancer 72(7):2083-2088; Birkeland E et al (2012) Br J Cancer 107(12):1997-2004; Vlajnic T et al (2011) Modern Pathology 24:1404-1412; Lundgren K et al (20120 Breast Cancer Res 14(2):R57). In such cases a strategy for effective cancer treatment is early detection and development of potent chemotherapeutic drugs that will selectively target protein(s) in the cancerous cells.

In this disclosure, we validate RFC40 as a non-receptor based molecular marker for breast cancers specifically, estrogen positive (ER positive), estrogen negative (ER negative), and progesterone, estrogen and human epidermal growth factor receptor 2-HER2 negative or triple negative breast cancers (TNBC). The assembly of the RFC complex is the first step in DNA elongation, committing the cell for DNA replication and hence over-expression of RFC40 could be an early event in the development of cancer and can prove to be a novel early diagnostic marker for the progression of cancer. Moreover, RFC40 may function as a non-invasive diagnostic tool since it can be detected in blood in blood cancers such as acute and chronic myeloid leukemia (Staber P B et al (2004) Oncogene 23(4):894-904; Merkerova M et al (2007) Neoplasma 54(6): 503-10).

Over-expression of any protein(s) in cancer can occur either due to (a) up-regulation of its mRNA, (b) increase in mRNA stability, (c) decrease in the protein degradation rate, and (d) increase in the translation rate. We propose that RFC40 protein and message is over-expressed in breast cancers, as illustrated in the schematic (FIG. 1). The present studies demonstrate that RFC40 protein is over-expressed in breast primary breast cancer cell lines as well as in patient breast cancer tissues.

We determined whether RFC40 is over-expressed in breast cancer using Western blot analysis for protein levels and quantitative RT-PCR of mRNA levels.

Western Blot Studies:

We performed western blot analyses for RFC40 protein with lysates obtained from non-cancerous mammary epithelial cells (MCF10A), ER positive breast cancer cells (MCF7), ER negative breast cancer cells (MDA-MB-231) and triple negative breast cancer-like cells (MDA-MB-468) using goat anti-RFC40 antibody (Bethyl Laboratories, TX, USA; Cat#A300-142A) as described previously (Ata H et al (2012) PLoS One 7(6):e39009). RFC40 was significantly up-regulated in all the breast cancer cells lines as compared to the non-cancerous breast cells (FIG. 2), suggesting that RFC40 is over-expressed in these breast cancer cells. β-Actin (Santa Cruz, Calif., USA; Cat# sc-47778) was used as the loading control.

To determine the expression of RFC40 protein in patient breast tissues, we used a 96-cores patient breast tissue microarray (BTMAs; Pantomics, Inc., CA, USA) containing 36 cases of breast cancers (20-ER positive and 15-ER negative) and 12 cases of normal, reactive and benign tumor tissues of the breast, in duplicates (FIG. 3). These BTMAs have been extensively used and well characterized in several studies (Moreira J M et al (2010) Mol Oncol 4(6):539-61; Unger K et al (2010) Endocr Relat Cancer 17(1):87-98). The tissues in the microarrays are fixed in 10% neutral buffered formalin for 24 to 48 hours. Tissue sections were cut fresh upon receiving an order. Pantomics provided the following information about each of the patient breast tumor samples on the BMTAs: (i) sex; (ii) age; (iii) pathology/location; (iv) grade; and (v) staining score for androgen (AR), estrogen (ER), progesterone (PR) receptors and human epidermal growth factor receptor (HER2) by immunohistochemical analyses (TABLE 1).

TABLE 1

| NO | Sex | Age | Organ | Pathology diagnosis | Grade | TNM | AR | ER | PR | HER 2 | Type |
|---|---|---|---|---|---|---|---|---|---|---|---|
| A1, B1 | F | 50 | Breast | Normal | | | 1%, + | 2%, ++ | 2%, +++ | — | NAT |
| A2, B2 | F | 47 | Breast | Normal/hyperplasia | | | 5%, + | 1%, + | 2%, +++ | — | NAT |
| A3, B3 | F | 40 | Breast | Normal/hyperplasia | | | — | — | 2%, ++ | — | NAT |

TABLE 1-continued

| NO | Sex | Age | Organ | Pathology diagnosis | Grade | TNM | AR | ER | PR | HER 2 | Type |
|---|---|---|---|---|---|---|---|---|---|---|---|
| A4, B4 | F | 32 | Breast | Normal/hyperplasia | | | 5%, ++ | 1%, ++ | — | — | NAT |
| A5, B5 | F | 50 | Breast | Granuloma | | | — | — | — | — | NAT |
| A6, B6 | F | 30 | Breast | Granuloma | | | — | — | — | — | NAT |
| A7, B7 | F | 50 | Breast | Fibrocystic changes | | | 5%, ++ | 1%, ++ | — | + | NAT |
| A8, B8 | F | 43 | Breast | Fibrocystic changes | | | 2%, + | 5%, + | — | — | NAT |
| A9, B9 | F | 25 | Breast | Fibroadenoma | | | 30%, ++~+++ | 30%, +++ | 15%, +++ | +~+++ | Benign |
| A10, B10 | F | 20 | Breast | Fibroadenoma | | | 20%, ++ | 30%, ++~+++ | 50%, +++ | + | Benign |
| A11, B11 | F | 23 | Breast | Fibroadenoma | | | 50%, ++ | 80%, +++ | 60%, +++ | + | Benign |
| A12, B12 | F | 50 | Breast | Fibroadenoma | | | 10%, + | 15%, ++ | 30%, +++ | + | Benign |
| C1, D1 | F | 43 | Breast | Invasive ductal carcinoma | I | TisN0M0 | — | — | — | +++ | Malignant |
| C2, D2 | F | 60 | Breast | Invasive ductal carcinoma | I | TisN0M0 | — | — | — | +++ | Malignant |
| C3, D3 | F | 37 | Breast | Invasive ductal carcinoma | I | TisN0M0 | 10%, ++ | 80%, ++~+++ | 50%, ++~+++ | +~++ | Malignant |
| C4, D4 | F | 41 | Breast | Lobular carcinoma in situ | I | TisN0M0 | — | 20%, ++ | 80%, +++ | + | Malignant |
| C5, D5 | F | 30 | Breast | Phyllodes sarcoma | | | — | — | — | — | Malignant |
| C6, D6 | F | 48 | Breast | Invasive ductal carcinoma | II | T1N0M0 | 50%, ++ | 60%, ++~+++ | 80%, +++ | — | Malignant |
| C7, D7 | F | 44 | Breast | Invasive ductal carcinoma | II~III | T1N0M0 | — | — | — | +++ | Malignant |
| C8, D8 | F | 61 | Breast | Invasive ductal carcinoma | II~III | T1N0M0 | 30%, +~++ | 100%, +++ | 50%, ++ | + | Malignant |
| C9, D9 | F | 40 | Breast | Invasive ductal carcinoma | II~III | T1N0M0 | 30%, +~++ | 60%, ++ | 80%, ++~+++ | ++ | Malignant |
| C10, D10 | F | 38 | Breast | Invasive ductal carcinoma | I~II | T1N0M0 | 15%, + | 15%, + | 30%, ++ | ++~+++ | Malignant |
| C11, D11 | F | 43 | Breast | Invasive ductal carcinoma | III | T2N0M0 | — | 20%, + | 30%, ++ | — | Malignant |
| C12, D12 | F | 48 | Breast | Invasive ductal carcinoma | II | T2N0M0 | — | 50%, +~++ | 80%, ++~+++ | — | Malignant |
| E1, F1 | F | 62 | Breast | Invasive ductal carcinoma | II~III | T2N0M0 | — | 90%, +++ | 60%, +++ | + | Malignant |
| E2, F2 | F | 47 | Breast | Invasive ductal carcinoma | II~III | T2N1M0 | — | 50%, ++ | 30%, ++ | + | Malignant |
| E3, F3 | F | 59 | Breast | Invasive ductal carcinoma | III | T2N0M0 | — | — | — | — | Malignant |
| E4, F4 | F | 72 | Breast | Invasive ductal carcinoma | I~II | T2N1M0 | — | — | — | — | Malignant |
| E5, F5 | F | 36 | Breast | Invasive ductal carcinoma | III | T2N0M0 | — | — | — | +++ | Malignant |
| E6, F6 | F | 48 | Breast | Invasive ductal carcinoma | II~III | T2N0M0 | — | — | — | +++ | Malignant |
| E7, F7 | F | 44 | Breast | Invasive ductal carcinoma | II~III | T2N0M0 | — | 50%, +~++ | — | — | Malignant |
| E8, F8 | F | 56 | Breast | Invasive ductal carcinoma | I~II | T2N0M0 | 5%, ++ | — | — | +++ | Malignant |
| E9, F9 | F | 50 | Breast | Invasive ductal carcinoma | II | T2N0M0 | — | — | — | ++~+++ | Malignant |
| E10, F10 | F | 50 | Breast | Invasive ductal carcinoma | II~III | T2N0M0 | 5%, ++ | 80%, +++ | 80%, +++ | + | Malignant |
| E11, F11 | F | 83 | Breast | Invasive ductal carcinoma | II | T2N0M0 | 10%, ++ | 80%, +++ | 50%, ++ | + | Malignant |
| E12, F12 | F | 64 | Breast | Invasive ductal carcinoma | III | T2N0M0 | — | 80%, ++~+++ | 20%, ++ | — | Malignant |
| G1, H1 | F | 58 | Breast | Invasive ductal carcinoma | II | T2N1M0 | — | — | — | — | Malignant |
| G2, H2 | F | 32 | Breast | Invasive ductal carcinoma | II~III | T3N0M0 | — | — | 20%, ++ | ++~+++ | Malignant |
| G3, H3 | F | 60 | Breast | Invasive ductal carcinoma | II~III | T3N0M0 | — | — | — | +++ | Malignant |
| G4, H4 | F | 58 | Breast | Invasive ductal carcinoma | III | T3N0M0 | — | — | — | — | Malignant |
| G5, H5 | F | 54 | Breast | Invasive ductal carcinoma | II~III | T3N3M0 | — | — | — | ++~+++ | Malignant |
| G6, H6 | F | 33 | Breast | Invasive ductal carcinoma | III | T3N0M0 | 20%, ++ | 80%, +++ | 50%, ++ | — | Malignant |
| G7, H7 | F | 51 | Breast | Invasive ductal carcinoma | II~III | T4N2MX | 30%, ++ | 80%, +++ | — | — | Malignant |
| G8, H8 | F | 55 | Breast | Invasive ductal carcinoma | III | T4N2MX | — | 80%, +++ | 50%, +++ | — | Malignant |
| G9, H9 | F | 36 | Breast | Invasive ductal carcinoma | II~III | T4N3MX | 30%, ++ | 60%, ++ | 60%, ++~+++ | +++ | Malignant |
| G10, H10 | F | 42 | Breast | Invasive ductal carcinoma | II~III | T4N3MX | 2%, + | 50%, +~++ | — | +~++ | Malignant |

TABLE 1-continued

| NO | Sex | Age | Organ | Pathology diagnosis | Grade | TNM | AR | ER | PR | HER 2 | Type |
|---|---|---|---|---|---|---|---|---|---|---|---|
| G11, H11 | F | 36 | Breast | Invasive ductal carcinoma | II | T4N2M0 | 5%, ++ | 90%, +++ | 100%, +++ | + | Malignant |
| G12, H12 | F | 36 | Breast | Invasive ductal carcinoma | I~II | T4N1M0 | — | — | — | +++ | Malignant |

The 96 cores patient BTMAs was subjected to immunohistochemical analyses (method in accordance with Golden T et al (2008) Biochim Biophys Acta 1782(4):259-70) using polyclonal anti-RFC40 (Bethyl Laboratories, TX, USA; Cat#A300-142A) followed by incubation with HRP-conjugated secondary antibodies for 1 h. Images of the stained sections were collected using Dako Cytomation system (FIG. 4A). The graph represents the RFC40 staining scores (intensity of staining×percentage of cells stained) in normal, estrogen positive (ER$^+$) and estrogen negative (ER$^-$) samples (FIG. 4B). The RFC40 staining scores were significantly increased in both positive and negative ER samples versus normal. We found that RFC40 protein was up-regulated by 7.9-fold in ER positive and 10.9-fold in ER negative breast tumors as compared to normal breast tissues (FIG. 4B), indicating that the RFC40 protein was over-expressed in patient breast cancers. Using this data we were able to correlate the grade and pathology of the breast cancers to the over-expression of RFC40 protein which may indicates that RFC40 is a prognostic indicator for therapy (TABLE 2).

TABLE 2

| NO | Pathology diagnosis | TNM | IHC for RFC40 | Type |
|---|---|---|---|---|
| A1, B1 | Normal | | 2, 1.8 | Normal |
| A2, B2 | Normal/hyperplasia | | 0.02, 0.03 | Normal |
| A4, B4 | Normal/hyperplasia | | 0.03, 0.08 | Normal |
| A7, B7 | Fibrocystic changes | | 0, 0 | Normal |
| A8, B8 | Fibrocystic changes | | 0, 0 | Normal |
| A9, B9 | Fibroadenoma | | 0.07, 0.11 | Normal |
| A10, B10 | Fibroadenoma | | 0.13, 0.08 | Normal |
| A11, B11 | Fibroadenoma | | 0, 0 | Normal |
| A12, B12 | Fibroadenoma | | 0, 0.006 | Normal |
| C3, D3 | Invasive ductal carcinoma | TisN0M0 | 13.2, 0.13 | ER+ve/HER2+ve |
| C4, D4 | Lobular carcinoma in situ | TisN0M0 | 4.2, no score | ER+ve/HER2+ve |
| C6, D6 | Invasive ductal carcinoma | T1N0M0 | 0.04, 0.15 | ER+ve/HER2-ve |
| C8, D8 | Invasive ductal carcinoma | T1N0M0 | 0.06, 0.034 | ER+ve/HER2+ve |
| C9, D9 | Invasive ductal carcinoma | T1N0M0 | 0.005, 0.005 | ER+ve/HER2+ve |
| C10, D10 | Invasive ductal carcinoma | T1N0M0 | 9, 2.9 | ER+ve/HER2+ve |
| C12, D12 | Invasive ductal carcinoma | T2N0M0 | 0.01, 0.94 | ER+ve/HER2-ve |
| E1, F1 | Invasive ductal carcinoma | T2N0M0 | 2.4, 5.6 | ER+ve/HER2+ve |
| E2, F2 | Invasive ductal carcinoma | T2N1M0 | 0.13, 1 | ER+ve/HER2+ve |
| E7, F7 | Invasive ductal carcinoma | T2N0M0 | 0.2, 0.05 | ER+ve/HER2-ve |
| E10, F10 | Invasive ductal carcinoma | T2N0M0 | 0.29, 1.2 | ER+ve/HER2+ve |
| E11, F11 | Invasive ductal carcinoma | T2N0M0 | 0.27, 0.04 | ER+ve/HER2+ve |
| E12, F12 | Invasive ductal carcinoma | T2N0M0 | 4.1, 1.7 | ER+ve/HER2-ve |
| G6, H6 | Invasive ductal carcinoma | T3N0M0 | 0, 0 | ER+ve/HER2-ve |
| G7, H7 | Invasive ductal carcinoma | T4N2MX | 1.6, 1.14 | ER+ve/HER2-ve |
| G8, H8 | Invasive ductal carcinoma | T4N2MX | 0, 6.7 | ER+ve/HER2-ve |
| G9, H9 | Invasive ductal carcinoma | T4N3MX | 0.042, 13.3 | ER+ve/HER2+ve |
| G10, H10 | Invasive ductal carcinoma | T4N3MX | 0.47, 0 | ER+ve/HER2+ve |
| G11, H11 | Invasive ductal carcinoma | T4N2M0 | 0, 0 | ER+ve/HER2+ve |
| C1, D1 | Invasive ductal carcinoma | TisN0M0 | 0.015, 0 | ER-ve/HER2+ve |
| C2, D2 | Invasive ductal carcinoma | TisN0M0 | 2.4, 4.5 | ER-ve/HER2+ve |
| C7, D7 | Invasive ductal carcinoma | T1N0M0 | 0.42, 0.43 | ER-ve/HER2+ve |
| E3, F3 | Invasive ductal carcinoma | T2N0M0 | 0.009, 0.01 | ER-ve/HER2-ve |
| E4, F4 | Invasive ductal carcinoma | T2N1M0 | 8.7, 0.01 | ER-ve/HER2-ve |
| E5, F5 | Invasive ductal carcinoma | T2N0M0 | 0.2, 0.06 | ER-ve/HER2+ve |
| E6, F6 | Invasive ductal carcinoma | T2N0M0 | 0.07, 0.03 | ER-ve/HER2+ve |
| E8, F8 | Invasive ductal carcinoma | T2N0M0 | 0.11, 0.005 | ER-ve/HER2+ve |
| E9, F9 | Invasive ductal carcinoma | T2N0M0 | 11.1, 9.6 | ER-ve/HER2+ve |
| G1, H1 | Invasive ductal carcinoma | T2N1M0 | 0, 0 | ER-ve/HER2-ve |
| G2, H2 | Invasive ductal carcinoma | T3N0M0 | 0.85, 22.2 | ER-ve/HER2+ve |
| G3, H3 | Invasive ductal carcinoma | T3N0M0 | 12.6, 3.8 | ER-ve/HER2+ve |
| G4, H4 | Invasive ductal carcinoma | T3N0M0 | 1.7, 0 | ER-ve/HER2-ve |
| G5, H5 | Invasive ductal carcinoma | T3N3M0 | 0.15, 0.06 | ER-ve/HER2+ve |
| G12, H12 | Invasive ductal carcinoma | T4N1M0 | 0.01, 0 | ER-ve/HER2+ve |

Figure 5:
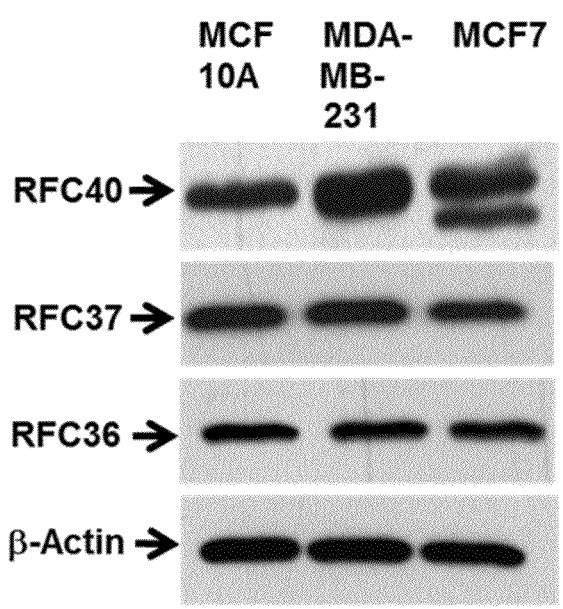
FIG. 5 MCF10A, MCF7 and MDA-MB-231 cells were lysed and 35 µg of total protein lysates were analyzed on 10% SDS-polyacrylamide gels. Protein expression of RFC40, RFC37 and RFC36 were examined by Western blot analyses. β-Actin was used as a loading control.

RFC40 was specifically over-expressed versus other RFC complex proteins. MCF10A, MCF7 and MDA-MB-231 cells were lysed and 35 μg of total protein lysates were analyzed on 10% SDS-polyacrylamide gels. Protein expression of RFC40, RFC37 (antibody from Santa Cruz Biotech, CA, USA; Cat# sc-28301) and RFC36 (antibody from Santa Cruz Biotech, CA, USA; Cat# sc-20997) was examined by Western blot analyses, with β-Actin used as a loading control (FIG. 5). Only RFC40 was increased in the breast cancer cell lines. The other RFC protein levels were comparable in all three lines tested, as was β-actin level.

mRNA Studies:

We performed quantitative RT-PCR for RFC40-mRNA using total RNA (t-RNA) extracted from MCF10A, MCF7, MDA-MB-231 and MDA-MB-468 cells as described previously (Ata H et al (2012) PLoS One 7(6):e39009). Assays for quantification of RFC40 and GAPDH mRNA expression were conducted on the iCycler (BioRad) using specific primers (all primers were purchased from Invitrogen) as follows: (a) for RFC40—Forward Primer: 5' ATGGAGGTGGAGGC-CGTCTGTG3' (SEQ ID NO:10; Tm=61.9° C.) and Reverse Primer: 5' CCTCTAGCCTGCTCACGGTGTCTTC3' (SEQ ID NO:11; Tm=61.4° C.); (b) for GAPDH—Forward Primer: 5' CTCATGACCACAGTCCATGCCATC3' (SEQ ID NO:12) and Reverse Primer: 5' CGGAAGGCCATGCCAGT-GAG3' (SEQ ID NO:13). RFC40, and GAPDH mRNA/cDNA amplification was programmed at 55° C. for 10 min for cDNA synthesis followed by 95° C. for 5 min (RT enzyme inactivation), and 40 cycles of 95° C. for 10 s, 60° C. for 30 s, and 72° C. for 30 s (data collection point). Melting curve analysis was subsequently conducted in order to verify the purity of the products. The fold increase in the mRNA levels were calculated from the crossing point (Ct) deviation of all the samples and normalized with GAPDH values. Amplified products were visualized on 4% agarose gels (FIG. 6A). Using ER positive and ER negative breast cancer cells, we found that the message for RFC40 was up-regulated by 3.86-fold in ER positive (MCF7) and 5.97-fold in ER negative (MDA-MB-231) breast cancer cell lines as compared to normal-cancerous (MCF10A) breast cells (FIG. 6B), respectively, suggesting that the RFC40 protein over-expression in the ER positive and negative breast cancer cells was due to up-regulation in the RFC40 message. Similarly, the message for RFC40 was significantly up-regulated by 2 fold in the TBNC-like breast cancer (MDA-MB-468) cells as compared to non-cancerous breast cells (FIG. 6C), suggesting that the RFC40 protein over-expression in the TNBC-like cells was due to up-regulation in RFC40 message.

Example 2

RFC40 is Localized in the Nucleus

It was determined that the pre-dominant localization of RFC40 in the nucleus is an indicator of the highly proliferative state of cancer cells. MCF10A, MCF7 and MDA-MB-231 cells were fixed and subjected to immunofluorescence microscopy using polyclonal anti-RFC40 antibody followed by incubation with Alexa-488-conjugated secondary antibodies for 1 h as described previously (Gupte R et al (2005) Cancer Biology and Therapy 4(4):429-437). Images of the stained sections were collected using a Nikon A1 microscope with Plan ×40/NA 0.25 Phi objective. Nuclear staining of RFC40 was more pronounced and significant in the breast cancer cells versus normal-cancerous breast cells (FIG. 7A). MCF10A, MCF7 and MDA-MB-231 cells were then subjected to flow cytometric analyses using DAPI (MCF10A) and PI (MCF7 and MDA-MB-231), respectively. Histograms representing the percent of cells in G1, S and G2 phases respectively demonstrate significantly higher percentage of S and G2 phase cells in the breast cancer cell lines as compared to non-cancerous breast cells (FIG. 7B), indicating that nuclear localization of RFC40 directly co-relates with increased proliferation in the breast cancer cells.

Figure 8:
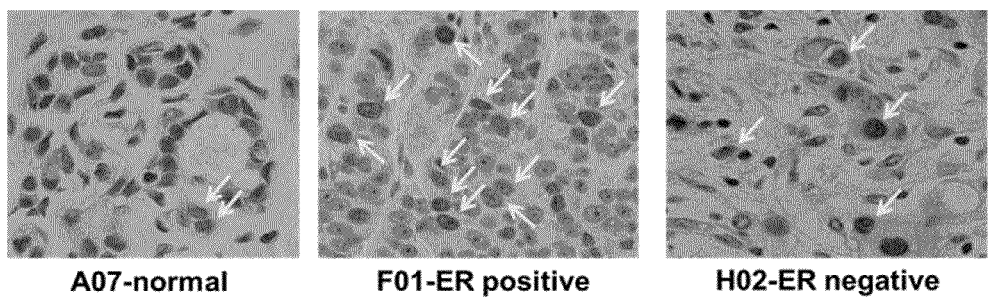

Immunohistochemical analyses of the 96-cores patient BTMA (as performed in Example 1 above) also demonstrated more intense nuclear staining of RFC40 protein in the ER positive and ER negative as compared to the normal breast tissue (FIG. 8), suggesting that increased nuclear localization of RFC40 may function as an indicator of progression and metastatic status of breast cancer.

Example 3

The RFC40 Gene is Amplified in Breast Cancer

Figure 9:
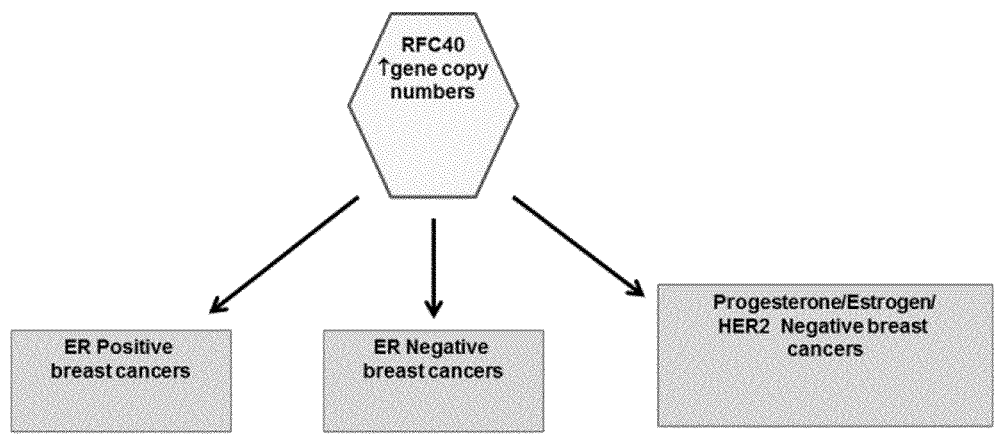
FIG. 9 is a schematic representation of RFC40 increased gene copy numbers in breast cancers, including in estrogen positive and estrogen negative and progesterone/estrogen/ HER2 negative breast cancers.

Over-expression of any protein(s) in cancer can occur due to aberrant amplification in its gene copy numbers in addition to up-regulation of its message and hence protein. Interestingly, amplification of RFC40 gene copy numbers as been previous demonstrated in glioblastomas (Nakahara Y et al (2004) Neuro Oncol 6(4):281-9; Suzuki T et al (2004) Brain Tumor Pathol 21(1):27-34). However, whether RFC40 gene copy numbers are increased in breast cancers has not been investigated. We propose that RFC40 gene copy number is amplified in breast cancers, as illustrated in the schematic (FIG. 9).

Figure 10:
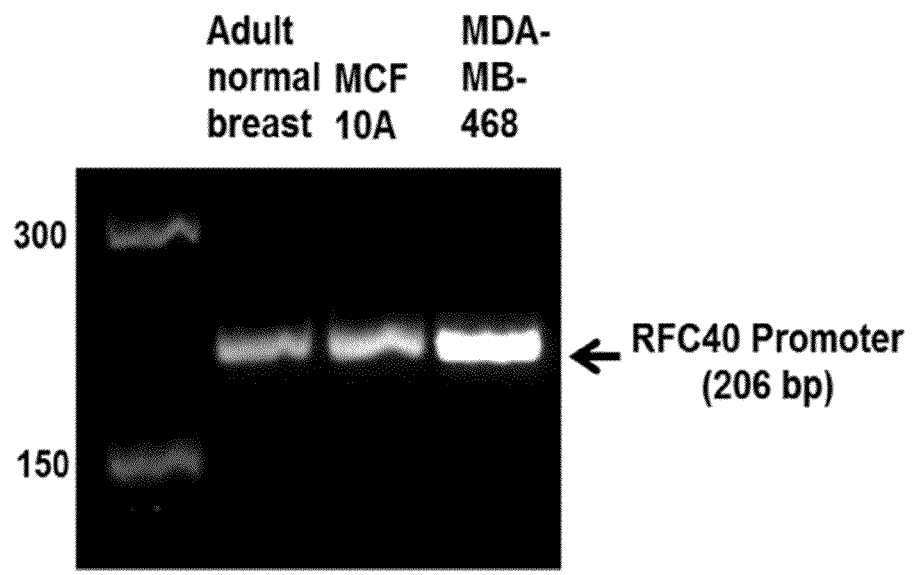
FIG. 10 Genomic DNA isolated from Adult normal breast tissue, MCF10A and MDA-MB-468 cells was subjected to PCR to amplify a 206 bp fragment of the RFC40 promoter. Amplified products were analyzed on 4% agarose gel.

We performed qualitative gene copy number analyses for the RFC40 promoter region located on the chromosome 7 at q11.23 position. We isolated genomic DNA from Adult normal breast tissue, MCF10A and MDA-MB-468 cells and performed qualitative PCR to amplify a 206 bp fragment on the RFC40 promoter and analyzed it on 4% agarose gel. The data suggested that the 206 bp fragment on the RFC40 promoter was significantly amplified in the MDA-MB-468 cells as compared to normal breast tissue and non-cancerous breast cells (FIG. 10). This data indicates that the copy numbers of RFC40 gene is amplified in the TNBC-like cells.

Figure 11:
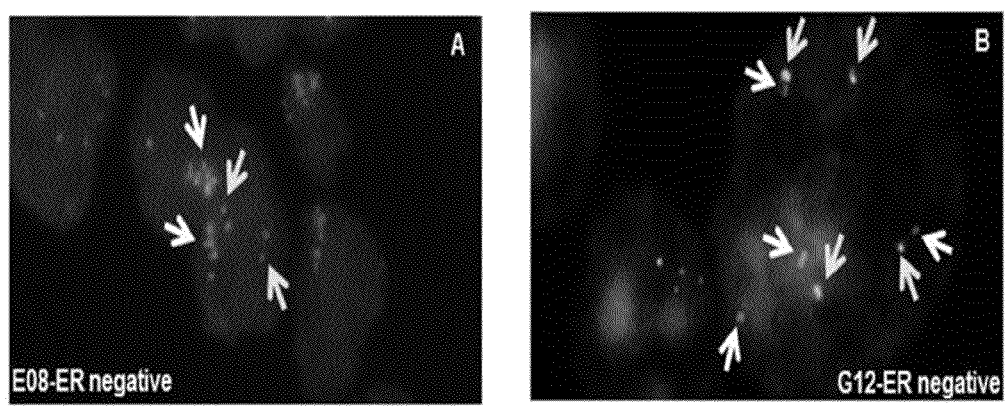
FIG. 11A-11B BTMAs were subjected to Fluorescent in-situ hybridization (FISH) using probe for RFC40 gene (RED; white arrows) on chromosome 7 and a centromeric enumeration probe for chromosome 7 (CEP7; GREEN; yellow arrows) as an internal control. Slides were imaged with Olympus BX61 microscope. (A) represents RFC40 gene amplification and (B) represents polysomy of chromosome 7.

We anticipated that FISH analyses would demonstrate that there is amplification of the RFC40 gene and/or polysomy of chromosome 7 in patient breast cancer tissues. To determine whether RFC40 gene copy numbers are amplified, Fluorescent in situ hybridization (FISH) in patient BTMAs (same methods as used in Example 1) was performed using a probe that hybridized to the RFC40 promoter region (RED; Empire Genomics, NY, USA) located on chromosome 7 at q11.23 position and an internal control—chromosome enumeration probe 7 (CEP7; GREEN; Vysis probes, Abbot, Ill., USA) as described previously (Ata H et al (2012) PLoS One 7(6): e39009). FISH stained slides were visualized by pathologists and the data was analyzed and scored following EGFR-based methods as described previously (Varella-Garcia M et al (2009) J Clin Pathol 62(11): 970-7). We first observed RFC40 gene copy number amplification (FIG. 11A) as well as polysomy for chromosome 7 (FIG. 11B) in several estrogen positive and negative breast tumor samples (TABLE 3), suggesting that the RFC40 gene is amplified in patient breast cancers.

TABLE 3

| NO | Pathology diagnosis | TNM | FISH SCORES RFC40 | CEP7 | FISH SCORES RFC40 | CEP7 | Type |
|---|---|---|---|---|---|---|---|
| A1, B1 | Normal | | A01-2 | 2 | B01-2 | 2 | Normal |
| A2, B2 | Normal/hyperplasia | | A02-2 | 2 | B02-2 | 2 | Normal |
| A4, B4 | Normal/hyperplasia | | A04-2 | 2 | B04-2 | 2 | Normal |
| A5, B5 | Granuloma | | A05-2 | 2 | B05-2 | 2 | Normal |
| A6, B6 | Granuloma | | A06-2 | 2 | B06-2 | 2 | Normal |
| A7, B7 | Fibrocystic changes | | A07-2 | 2 | B07-2 | 2 | Normal |
| A8, B8 | Fibrocystic changes | | A08-2 | 2 | B08-2 | 2 | Normal |
| A10, B10 | Fibroadenoma | | A10-2 | 2 | B10-2 | 2 | Normal |
| A11, B11 | Fibroadenoma | | A11-2 | 2 | B11-2 | 2 | Normal |
| A12, B12 | Fibroadenoma | | A12-2 | 2 | B12-2 | 2 | Normal |
| C3, D3 | Invasive ductal carcinoma | TisN0M0 | C03-2 | 2 | D03-NA | NA | ER +ve/HER2+ve |
| C4, D4 | Lobular carcinoma in situ | TisN0M0 | C04-2 | 2 | D04-3 | 3 | ER +ve/HER2+ve |
| C6, D6 | Invasive ductal carcinoma | T1N0M0 | C06-5 | 3 | D06-4 | 4 | ER +ve/HER2−ve |
| C8, D8 | Invasive ductal carcinoma | T1N0M0 | C08-2 | 2 | D08-2 | 2 | ER +ve/HER2+ve |
| C9, D9 | Invasive ductal carcinoma | T1N0M0 | C09-2 | 2 | D09-2 | 2 | ER +ve/HER2+ve |
| C10, D10 | Invasive ductal carcinoma | T1N0M0 | C10-NA | NA | D10-3 | 3 | ER +ve/HER2+ve |
| C12, D12 | Invasive ductal carcinoma | T2N0M0 | C12-6 | 6 | D12-3 | 3 | ER +ve/HER2−ve |
| E1, F1 | Invasive ductal carcinoma | T2N0M0 | E01-2 | 2 | F01-NA | NA | ER +ve/HER2+ve |
| E2, F2 | Invasive ductal carcinoma | T2N1M0 | E02-3 | 3 | F02-2 | 2 | ER +ve/HER2+ve |
| E7, F7 | Invasive ductal carcinoma | T2N0M0 | E07-2 | 2 | F07-2 | 2 | ER +ve/HER2−ve |
| E10, F10 | Invasive ductal carcinoma | T2N0M0 | E10-2 | 2 | F10-3 | 3 | ER +ve/HER2+ve |
| E11, F11 | Invasive ductal carcinoma | T2N0M0 | E11-2 | 2 | F11-2 | 2 | ER +ve/HER2+ve |
| E12, F12 | Invasive ductal carcinoma | T2N0M0 | E12-2 | 2 | F12-2 | 2 | ER +ve/HER2−ve |
| G6, H6 | Invasive ductal carcinoma | T3N0M0 | G06-2 | 2 | H06-2 | 2 | ER +ve/HER2−ve |
| G7, H7 | Invasive ductal carcinoma | T4N2MX | G07-4 | 4 | H07-4 | 4 | ER +ve/HER2−ve |
| G8, H8 | Invasive ductal carcinoma | T4N2MX | G08-2 | 2 | H08-2 | 2 | ER +ve/HER2−ve |
| G9, H9 | Invasive ductal carcinoma | T4N3MX | G09-3 | 3 | H09-3 | 3 | ER +ve/HER2+ve |
| G10, H10 | Invasive ductal carcinoma | T4N3MX | G10-3 | 3 | H10-4 | 4 | ER +ve/HER2+ve |
| G11, H11 | Invasive ductal carcinoma | T4N2M0 | G11-2 | 2 | H11-3 | 3 | ER +ve/HER2+ve |
| C1, D1 | Invasive ductal carcinoma | TisN0M0 | C01-2 | 2 | D01-4 | 4 | ER −ve/HER2+ve |
| C2, D2 | Invasive ductal carcinoma | TisN0M0 | C02-2 | 2 | D02-4 | 4 | ER −ve/HER2+ve |
| C7, D7 | Invasive ductal carcinoma | T1N0M0 | C07-5 | 5 | D07-4 | 4 | ER −ve/HER2+ve |
| E3, F3 | Invasive ductal carcinoma | T2N0M0 | E03-2 | 2 | F03-2 | 2 | ER −ve/HER2−ve |
| E4, F4 | Invasive ductal carcinoma | T2N1M0 | E04-5 | 4 | F04-2 | 2 | ER −ve/HER2−ve |
| E5, F5 | Invasive ductal carcinoma | T2N0M0 | E05-2 | 2 | F05-2 | 2 | ER −ve/HER2+ve |
| E6, F6 | Invasive ductal carcinoma | T2N0M0 | E06-5 | 5 | F06-4 | 4 | ER −ve/HER2+ve |
| E8, F8 | Invasive ductal carcinoma | T2N0M0 | E08-6 | 2 | F08-5 | 2 | ER −ve/HER2+ve |
| E9, F9 | Invasive ductal carcinoma | T2N0M0 | E09-2 | 2 | F09-2 | 2 | ER −ve/HER2−ve |
| G1, H1 | Invasive ductal carcinoma | T2N1M0 | G01-2 | 2 | H01-3 | 3 | ER −ve/HER2−ve |
| G2, H2 | Invasive ductal carcinoma | T3N0M0 | G02-2 | 2 | H02-2 | 2 | ER −ve/HER2−ve |
| G3, H3 | Invasive ductal carcinoma | T3N0M0 | G03-5 | 5 | H03-3 | 3 | ER −ve/HER2+ve |
| G4, H4 | Invasive ductal carcinoma | T3N0M0 | G04-2 | 2 | H04-2 | 2 | ER −ve/HER2−ve |
| G5, H5 | Invasive ductal carcinoma | T3N3M0 | G05-4 | 4 | H05-6 | 6 | ER −ve/HER2+ve |
| G12, H12 | Invasive ductal carcinoma | T4N1M0 | G12-5 | 5 | H12-4 | 4 | ER −ve/HER2+ve |

Example 4

Over-Expression of RFC40 Confers Growth Advantages to Non-Cancerous Breast Epithelial Cells RFC40 is required for DNA replication, DNA checkpoint repair, genomic stability and sister chromatid cohesion in the cell (Majka J et al (2004) Prog Nucleic Acid Res Mol Biol 78: 227-260; Petronczki M et al (2004) J Cell Sci 117(Pt 16): 3547-3559). Additionally, we have recently discovered that RFC40 is required for accurate chromosomal segregation and completion of cell division after mitosis in proliferating neonatal rat cardiac myocytes, suggesting a role for RFC40 in mitosis and cytokinesis (Ata H et al (2012) PLoS One 7(6): e39009). We also observed that inhibition of endogenous RFC40 in proliferating neonatal rat cardiac myocytes causes cell death. Consistently, it has been demonstrated that deletion of RFC40 gene is embryonically lethal in yeast (Cullmann G et al (1995) Mol Cell Biol 15(9):4661-71). Taken together these findings suggest that RFC40 is required for cell proliferation. Since unrestricted proliferation, as observed in the cancerous cells, requires a continuous supply of the DNA replication proteins, it is possible that over-expression of RFC40 protein may be associated with deregulation of growth control, leading to malignant transformation. Consistently, we have observed that RFC40 protein and message is up-regulated and its gene copy numbers amplified in ER positive and negative breast cancers (see Examples above). Over-expression of RFC40 may be responsible for inducing proliferative advantages and causing oncogenic transformation to non-cancerous cells.

Figure 12:
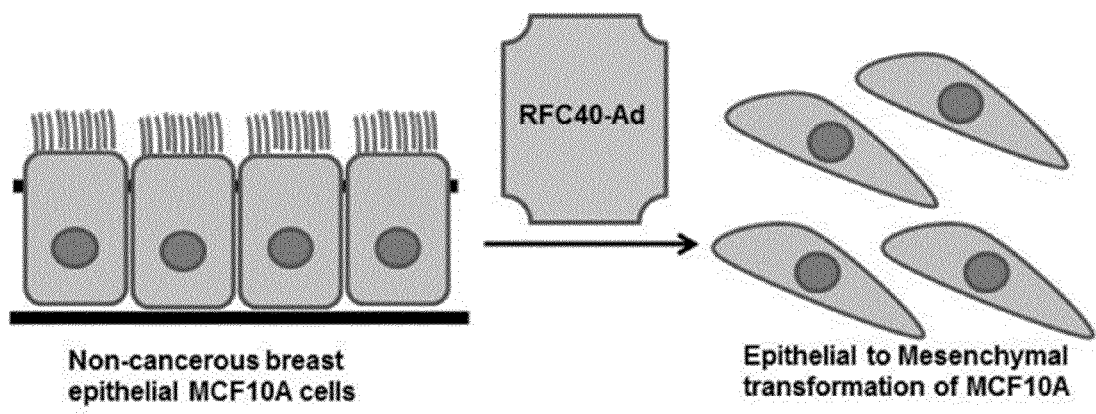
FIG. 12 Schematic representation of the oncogenic properties of RFC40 protein. Over-expression of RFC40 in non-cancerous breast epithelial cells lead to oncogenic transformation of these cells with changes from epithelial to stromal or mesenchymal phenotype.

We sought to determine whether over-expression of RFC40 can induce oncogenic transformation of non-cancerous breast epithelial breast cells by investigating the phenotypic transitions that are hallmarks of oncogenic transformations such as epithelial to mesenchymal transition as illustrated in the schematic (FIG. 12). Specifically we will determine the down-regulation of epithelial marker proteins and over-expression of mesenchymal marker proteins accompanied by epitheloid to stromal phenotypic changes and growth factor-independent proliferation (Overholtzer M et al (2006) Proc Natl Acad Sci USA 103(33):12405-10; Kalluri R and Weinberg R A (2009) J Clin Invest 119(6):1420-8). In these studies, we over-expressed the RFC40 gene in non-cancerous breast epithelial cells (MCF10A) and determined (I) the percentage of S-phase cells and cell number analyses to determine whether over-expression of RFC40 can cause increase in the cell numbers; and (II) changes in cell morphogenesis.

Figure 13:
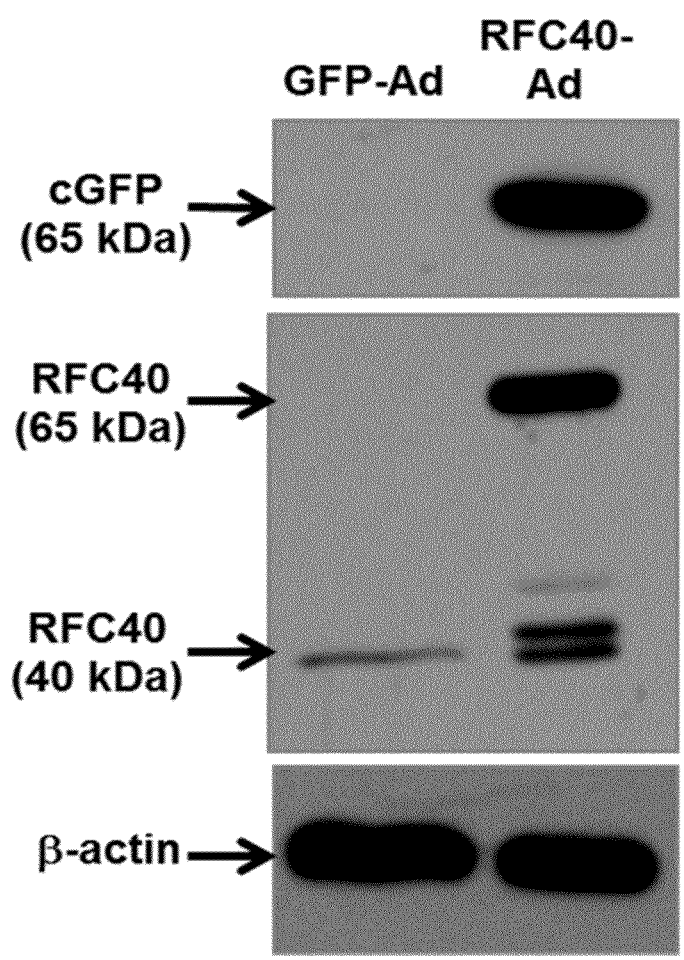
FIG. 13 Western blot analyses for cGFP, RFC40 and β-actin using lysates obtained from GFP-Ad and RFC40-Ad transfected MCF10 cells.
Figure 14:
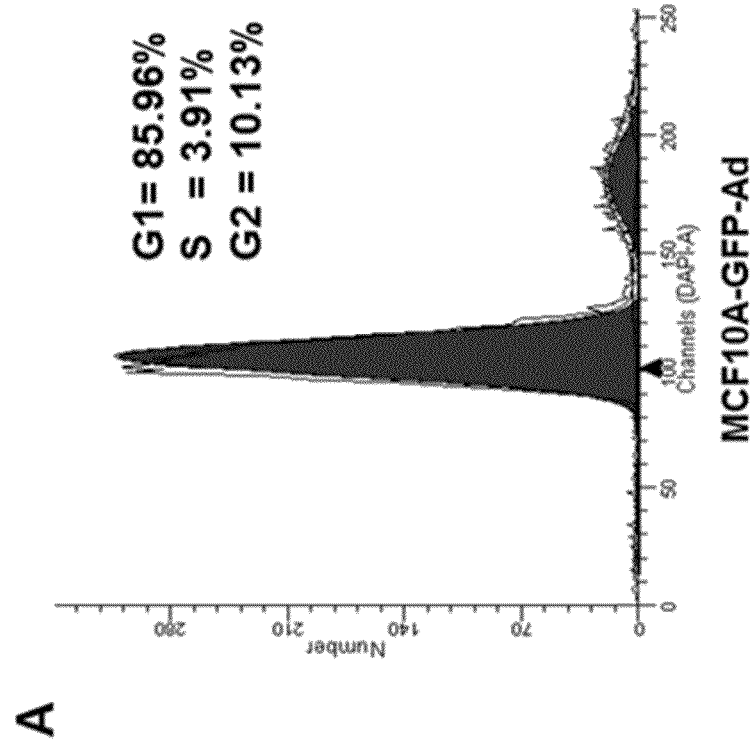
FIG. 14A-14C Univariate FASC analysis of cellular DNA content in GFP-Ad and RFC40-Ad over-expressed MCF10A cells. A representative histogram for GFP-Ad (A) and RFC40-Ad over-expressed (B) MCF10A cells with the percentage of cells in G1, S and G2-phases respectively, is shown. (C) Western blot analyses for Cyclin D1, Cyclin A and Cyclin B1 using lysates obtained from GFP-Ad and RFC40-Ad transfected MCF10 cells.
Figure 14:
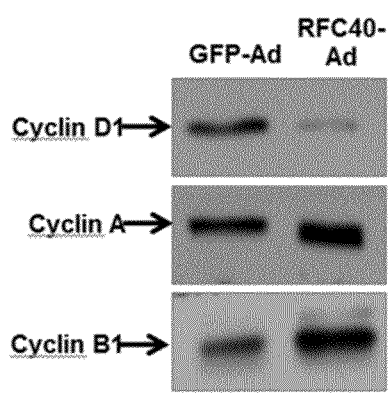

To determine whether over-expression of RFC40 influences the number of cells in the S-phase, we cloned full-length RFC40 gene in-frame with Green Fluorescent Protein in adenoviral vector (RFC40-Ad) and transiently transfected it in MCF10A cells for 48 hr (FIG. 13) as described previously (Gupte R S et al (2011) Antioxid Redox Signal 14(4): 543-58). Fluorescent assisted cell sorting (FACS) analysis was performed to determine the percentage of S-phase cells using univariate analysis of cellular DNA content in control (GFP-Ad pDNA alone; GFP-Ad) and RFC40 over-expressed MCF10A cells as described previously (Pozarowski P and Darzynkiewicz Z (2004) Methods Mol Biol 281: 301-11). We found that there was increase in the percentage of S-phase cells from 3.91% in GFP-Ad (FIG. 14A) to 19.54% in RFC40-Ad over-expressed MCF10A cells (FIG. 14B), with concomitant increase in the percentage of G2/M phase cells from 10.13% (in GFP-Ad; (FIG. 14A) to 19.77% (in RFC40-Ad; (FIG. 14B) and decrease in the G1-phase cells from 85.96% (in GFP-Ad; (FIG. 14A) to 60.69% (in RFC40-Ad; (FIG. 14B), respectively. Consistently, we observed up-regulation of Cyclin A (S-phase marker) and Cyclin B1 (G2/M-phase marker) and down-regulation of Cyclin D1 (G1-phase marker) in the RFC40-Ad transfected MCF10A cells as compared to GFP-Ad (FIG. 14C), suggesting that over-expression of RFC40 in MCF10A cells promoted an increase in the number of S-phase cells similar to those seen in cancerous cells.

To further assess over-expression of RFC40 and increase in cell number, we transiently transfected MCF10A cells as described above and measured the total number of cells using a hemocytometer. We found that there was 42.8% increase in the relative cell numbers in RFC40-Ad transfected MCF10A cells as compared to GFP-Ad (data not shown), suggesting that over-expression of RFC40 in MCF10A cells promoted proliferation of RFC40-Ad transfected MCF10A cells.

To determine whether over-expression of RFC40 induces changes in cell morphogenesis, we transiently transfected MCF10A cells as described above, and performed DIC microscopy using a Nikon Eclipse TE2000-E (20×) and found that MCF10A cells transfected with RFC40-Ad appeared to lose cell to cell contact and display a stromal-like phenotype (FIG. 15B) as compared to the epithelial-type phenotype of GFP-Ad transfected MCF10A cells that grew in monolayers (FIG. 15A).

Figure 16:
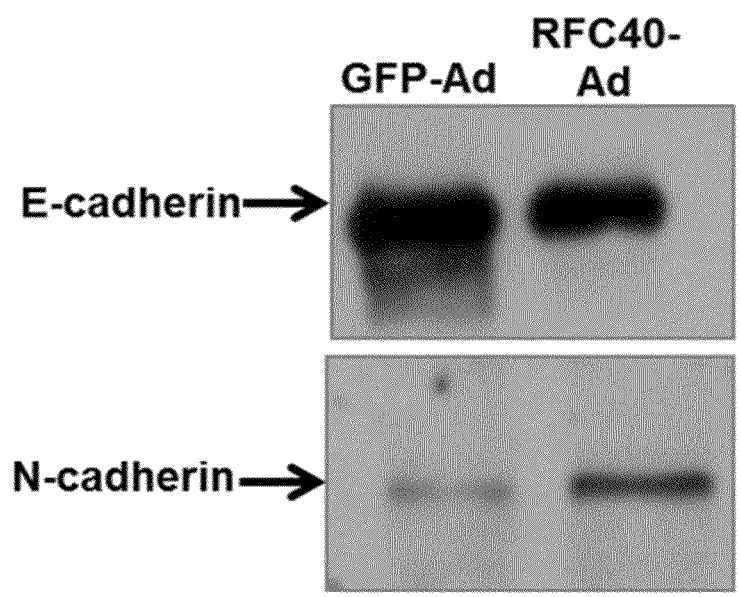
FIG. 16 Western blot analyses for E-cadherin and N-cadherin using lysates obtained from GFP-Ad and RFC40-Ad transfected MCF10 cells.

Western blot analysis was then performed to determine whether over-expression of RFC40 in MCF10A cells promotes the epithelial to mesenchymal transition. Western blot analyses were performed for E-cadherin (down-regulation/loss of epithelial marker) and N-cadherin (gain of mesenchymal markers). We found that E-cadherin was down-regulated whereas N-cadherin was up-regulated in RFC40-Ad transfected MCF10A cells as compared to GFP-Ad (FIG. 16), indicating that over-expression of RFC40 induced growth advantages to non-transformed breast epithelial cells and promoted epithelial to mesenchymal transition.

Example 5

RFC40 as a Therapeutic Target

Breast cancer accounts for 18% of all cancers in women, making it the foremost cause of cancer-related deaths in women (McPherson K et al (2000) BMJ 321(7261):624-8). Early diagnosis and treatment of breast cancer could play a monumental role in reducing deaths (Misek D E and Kim E H (2011) Int J Proteomics 2011:343582). Most of the drugs available for the treatment of breast cancers target either the endocrine (estrogen; ER) or growth factor ((ErbB-1, ErbB-2 [human epidermal growth factor receptor 2; HER2], ErbB-3 and ErbB-4) receptors for therapy, however, emerging resistance to endocrine and therapies targeted against HER2 receptors have created a dire need for identification of molecular targets that are non-receptor based and directly involved in the proliferation of the cancer cells (Normanno N et al (2005) Endocr Relat Cancer 12(4):721-47; Normanno N et al (2009) Endocr Relat Cancer 16(3):675-702). Triple Negative breast cancer (TNBC), a subtype of breast cancer where tumors and cells lack the estrogen, progesterone as well as the human epidermal growth factor receptor 2 which will not respond to any traditional therapies, is emerging as the most aggressive of breast cancers that can metastasis beyond the breast and are more likely to recur after treatment.

Prior to the studies in the above Examples, the role of RFC40 in breast cancer had not been assessed. The present studies demonstrate the over-expression of RFC40 protein and RFC40 gene amplification in estrogen positive and negative breast cancers and its role in cell proliferation in cancer. The direct correlation between RFC40 over-expression and the progression and metastatic status of breast cancer makes it an effective candidate for a novel non-receptor based molecular target for breast cancers. Interestingly, since the DNA replication machinery does not change irrespective of the tissue type or the extracellular stimuli, such as endocrine and growth receptors, identifying molecular targets involved in DNA replication such as RFC40 may offer a global treatment for all subtypes of breast cancer. Additionally, since there are no reported polymorphisms for the RFC40 gene/protein, target-based therapy against this protein will cover breast cancer treatment across all ethnic groups. Furthermore, its over-expression in choriocarcinoma (Cui J Q et al (2004) Chinese J Cancer 23:196-200) and cancers of various tissues such as acute and chronic myeloid leukemia (Staber P B et al (2004) Oncogene 23(4):894-904; Merkerova M et al (2007) Neoplasma 54(6):503-10), nasopharyngeal cancer (Xiong S et al (2011) Med Oncol 28(Suppl 1):S341-8), and glioblastomas (which were accidental findings of their respective studies) (Nakahara Y et al (2004) Neuro Oncol 6(4):281-9; Suzuki T et al (2004) Brain Tumor Pathol 21(1):27-34), makes RFC40 a novel and universal molecular target for anti-cancer drug therapy.

Furthermore, and without intending to be constrained by any particular theory, unlike other conventional drugs that globally bind to DNA directly, causing inhibition of DNA synthesis as well as DNA repair, targeting RFC40 for drug development would inhibit the formation of the RFC complex, thereby stalling DNA replication without damaging the DNA itself. This approach would provide a novel alternative to conventional drugs by significantly minimizing the off-target effects on DNA as well as other proteins involved in DNA repair.

siRNA and miRNA studies: The data provided herein and below (Example 6 and 7) indicate that inhibition of endogenous RFC40 by siRNA or miRNAs is onco-specific and occurs only in the cancerous cells (probably due to up-regulated levels of RFC40-mRNA in the highly proliferative cancer cell population) as compared to normal cells. This establishes the unique possibility of inhibition of RFC40 specifically in cancerous cells, thus offering selectivity and specificity for therapeutic intervention. Specifically targeting endogenous RFC40 by blocking translation using siRNA, miRNA, as well as via antisense or ribozyme approaches provides a new and directed approach to breast cancer, whether estrogen sensitive, estrogen resistant or TNBC, and a means to inhibit cell division and growth of cancer cells or tumors, via inhibiting or blocking DNA replication specifically in cancer or tumor cells.

Small molecule compounds: Previous studies have demonstrated that RFC40 interacts directly with RIα, which is a regulatory subunit of Protein Kinase A (PKA), and that inhibition of the interaction between RFC40 and RIα, which is required to transport RFC40 into the nucleus, results in G1 arrest (Gupte R et al (2005) Cancer Biology and Therapy 4(4):429-437). RIα is a regulatory subunit associated with the PKAI or RI form of PKA, which is a versatile serine-threonine kinase that mediates cAMP dependent regulation for a variety of cellular processes. Taking into consideration the above examples demonstrating the link between RFC40 and breast cancer and increased expression of RFC40 in breast cancer, we hypothesized that compounds that will disrupt the RFC40-RIα interaction, thereby preventing transport of RFC40 to the nucleus where it is required for activity, will affect the cell survival of breast cancer cells.

To assess this, we have treated estrogen positive breast cancer cells (MCF7) with indole-3-carbinol compounds and subjected the cell lysates to immunoprecipitation experiments using anti-RFC40 antibody, using methods as described previously (Gupte R S et al (2005) Cell Cycle 4(2): 323-329). We found that the RFC40-RIα interaction was almost completely abolished in the indole-3-carbinol treated MCF7 cells as compared to the control (data not shown). Indole-3-Carbinol (I3C) is a compound found in cruciferous vegetables including broccoli, cabbage and cauliflower. Several studies demonstrate that it can cause cell cycle arrest and apoptosis in cancer cell lines (Wattenburg L W (1978) Cancer Res 38:1410-1413; Cover C M et al (1999) Cancer Res 59:1244-1251; Cover C M et al (1998) J Biol Chem 273: 3838-3847; Chinni S R (2002) Clin Cancer Res 8:1228-1236; Chen D Z et al (2001) J Nutr 131:3294-3302; Hong C et al (2002) Biochem Pharmacol 63(6):1085-1097; Nachshon-Kedmi, M et al (2003) Food Chem Toxicol 41(6):745-752; Choi H S et al (2010) 48(3):883-890). Hsu et al. demonstrated that indole-3-carbinol induces a G1 growth arrest of human prostate cancer cells (Hsu J et al (2006) Biochem Pharmacol 72(12):1714-1723).

Other approaches to utilize the RFC40 link in breast cancer for treatment via inhibiting the RIα interaction with RFC40, or to directly inhibit RFC40 activity include cAMP modulators and inhibitors of CDK/cyclin E complex, such as olomoucine. Elevated intracellular cAMP levels exert transcriptional/post-transcriptional effects on mRNA levels and a translation effect on the protein expressions of both RFC40 and RIα, thereby increasing the amount of the RIα-RFC40 complex formation and hence promoting the nuclear transport of RFC40 by RIα (Gupte R et al (2006) Exper Cell Res 312:796-806). Once in the nucleus, dissociation of the RIα-RFC40 complex requires phosphorylation of RIα by the CDK2/Cyclin E complex, as evidenced by the inability of the RIα-RFC40 complex to dissociate in the presence of olomoucine (2-(2-hydroxyethylamino)-6-benzylamino-9-methylpurine), a competitive inhibitor (ATP-binding site) or cyclin dependent kinases, particularly cdc2/cyclinB, cdk2/cyclin A and cdk2/cyclinE. Inability of the RIα-RFC40 complexed proteins to dissociate efficiently from each other further affects the ability of RFC40 to form a complex with RFC37 and hence the functional RFC pentamer, subsequently affecting DNA synthesis/replication. Thus olomoucine, or the more efficient inhibitor roscovitine, have applicability in treatment or alleviation of breast cancer, particularly via altering RIα-RFC40 complex.

Figure 6:
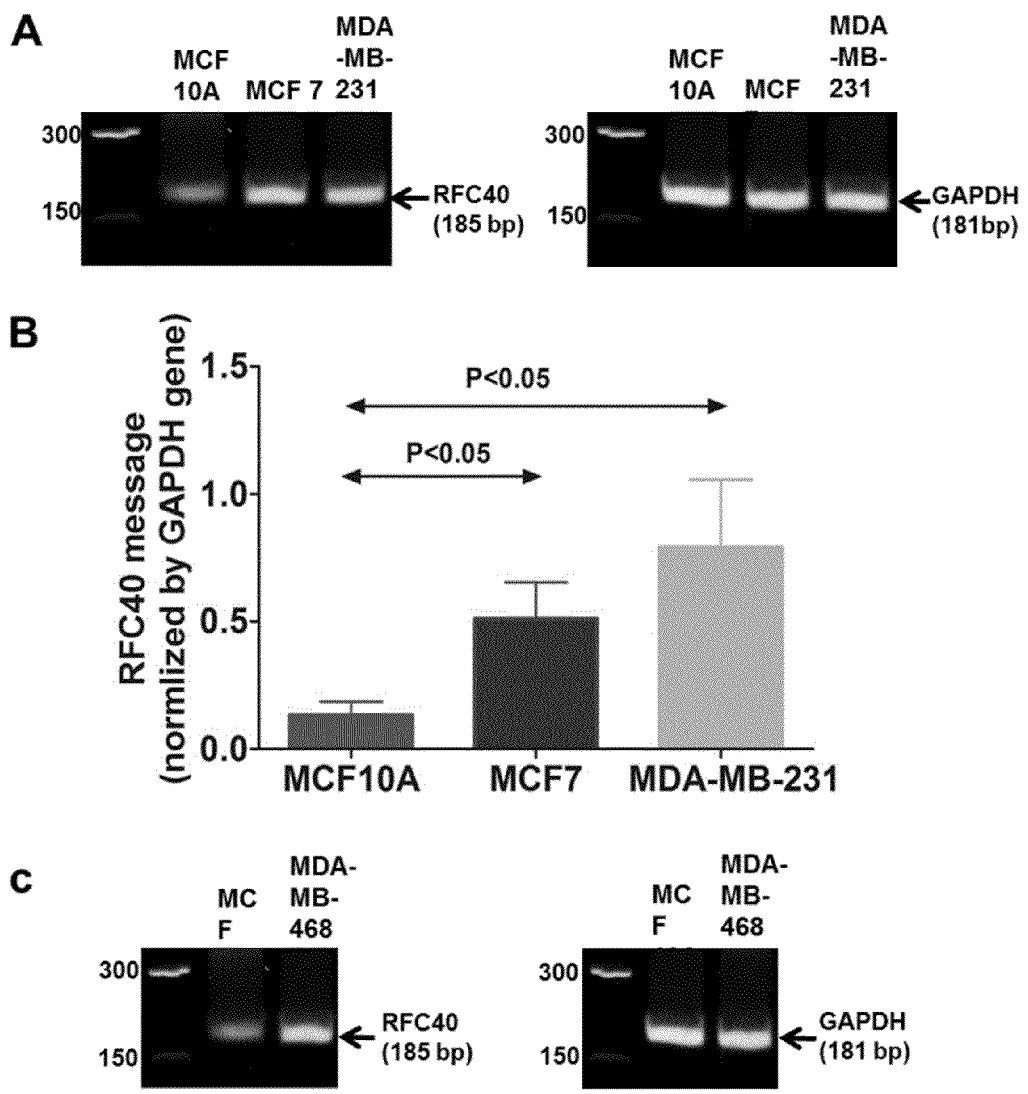
FIG. 6A-6C Total RNA was extracted from MCF10A, MCF7 and MDA-MB-231 cells and 50 ng of the t-RNA isolated from each of these samples (n=2) was subjected to real-time one-step-RT-PCR. (A) and (C) Assays for quantification of RFC40 and GAPDH mRNA expression were conducted on the Cycler and the amplified products were visualized on 4% agarose gels at the end of each run: (A) depicts results for MCF10A, MCF7 and MDA-MB-231 cells, (C) depicts results for MCF10A and MDA-MB-468 cells. (B) Graphs represent the increases in the mRNA levels calculated from the crossing point deviation of all the samples and normalized with GAPDH values.
Figure 7:
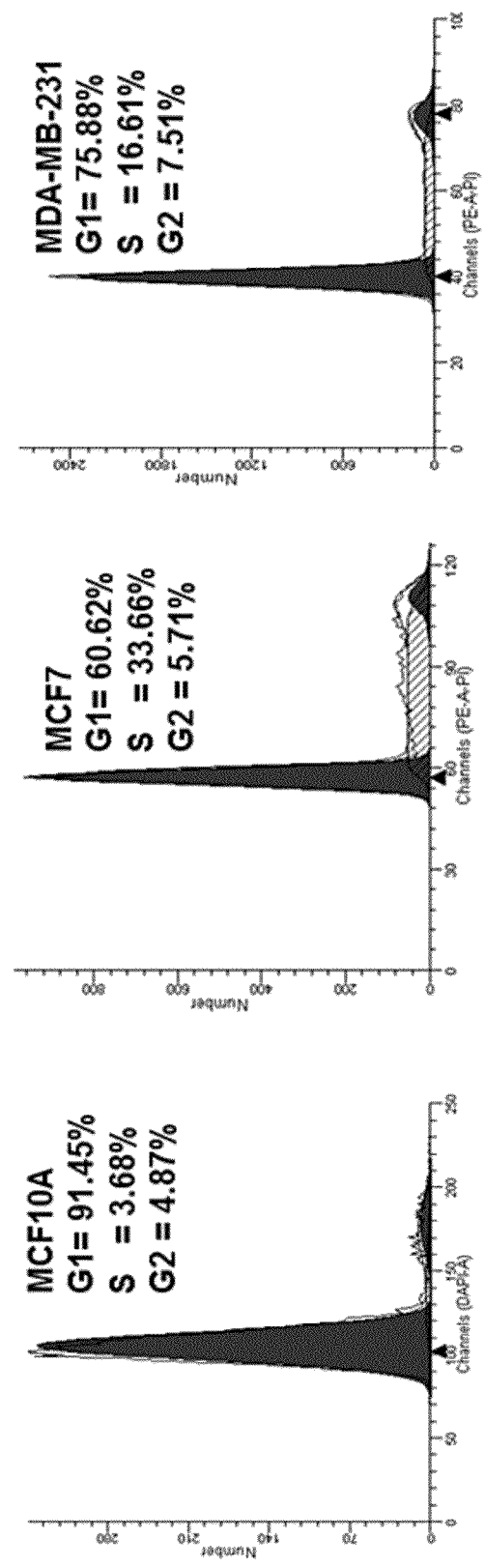
FIGS. 7A and 7B (A) MCF10A and MDA-MB-231 cells were fixed and subjected to immunofluorescence microscopy using polyclonal anti-RFC40 followed by incubation with Alexa-488-conjugated secondary antibodies for 1 h. Images of the stained sections were collected using an Nikon A1 microscope with Plan x40/NA 0.25 Phi objective. (B) MCF10A, MCF7 and MDA-MB-231 cells were subjected to flow cytometric analyses using DAPI (MCF10A) and PI (MCF7 and MDA-MB-231), respectively. Histograms represent the percent of cells in G1, S and G2 phases respectively.
Figure 17:
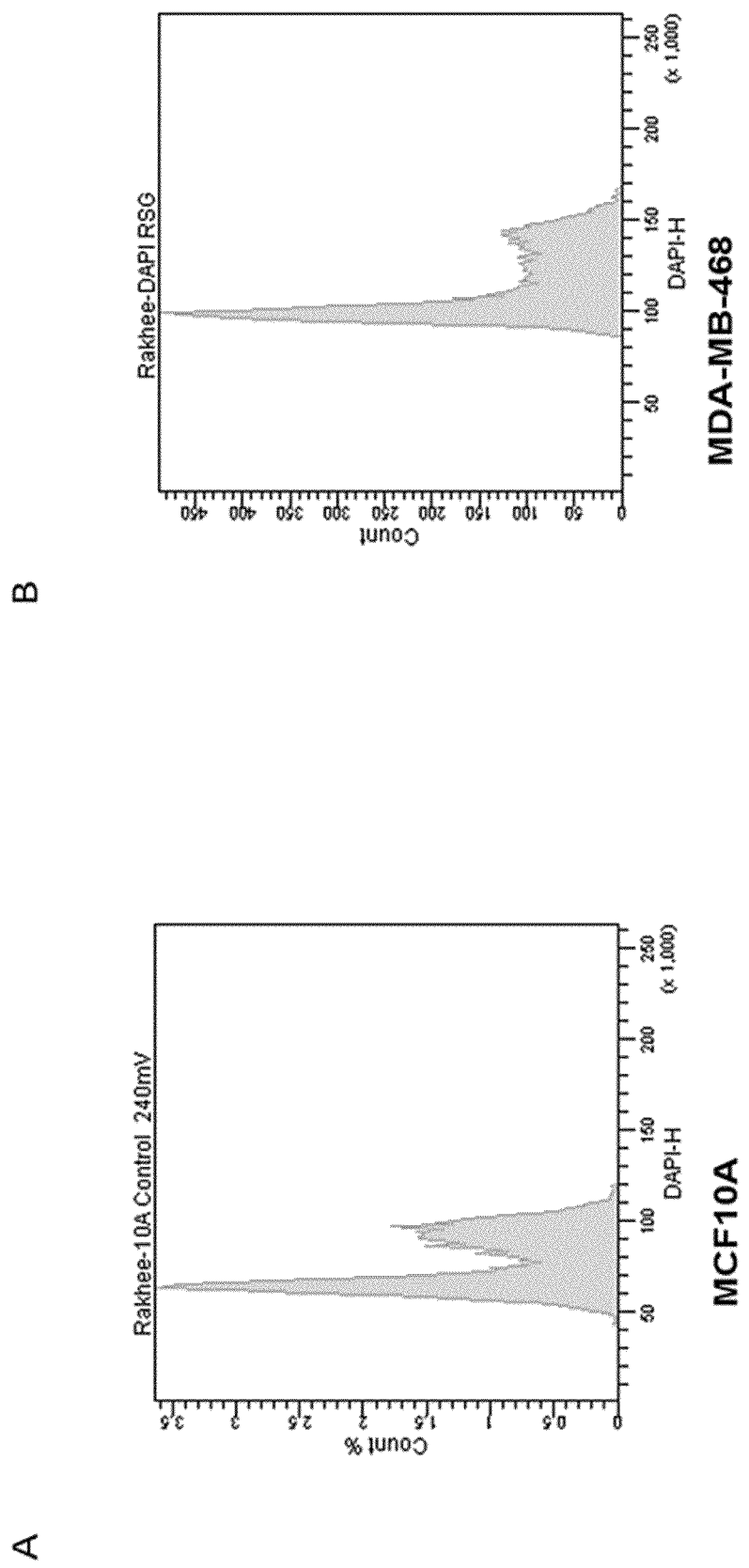
FIGS. 17A and 17B Univariate analysis of cellular DNA content in MCF10A and MDA-MB-468 cells: MCF10A and MDA-MB-468 cells ($1 \times 10^6$) were subjected to flowcytometric analysis using 4',6'-diamidino-2-phenylindole (DAPI) as described previously. A representative histogram for MCF10A (A) and MDA-MB-468 (B) is shown.

Example 6 siRNA Inhibition of Endogenous RFC40 Results in Cell Death in Breast Cancer Cells Taking into consideration the above studies and results, it was then predicted that inhibition of endogenous RFC40 can inhibit cell survival/proliferation and cause either cycle arrest or cell death in cancer cells, particularly breast cancer cells. Inhibition of endogenous RFC40 by RFC40-siRNA would target the RFC40 gene in both normal as well as the cancerous cells, since it is also expressed in normal breast cells. However, univariate analysis of cellular DNA content in MCF10A and MDA-MB-468 (FIG. 17) cells and MCF7 and MDA-MB-231 (FIG. 7) cells using methods described previously (Staber P B et al (2004) Oncogene 23(4):894-904), demonstrated that the rate of DNA replication is relatively low (approximately 3% S-phase cells) in MCF10A cells (FIGS. 7 & 17) as compared to MCF7 cells (approximately 33.6% S-phase cells; FIG. 7), MDA-MB-231 cells (approximately 16.6% S-phase cells; FIG. 7) and MDA-MB-468 cells (approximately 20-30% S-phase cells; FIG. 17) and also that the RFC40 message is maintained at low levels in the MCF10A cells as compared to MCF7, MDA-MB-231 and MDA-MB-468 cells (FIG. 6). Hence, we anticipated that the effect of RFC40-siRNA on MCF10A cells would be less pronounced than that in the cancerous cells.

Figure 15:
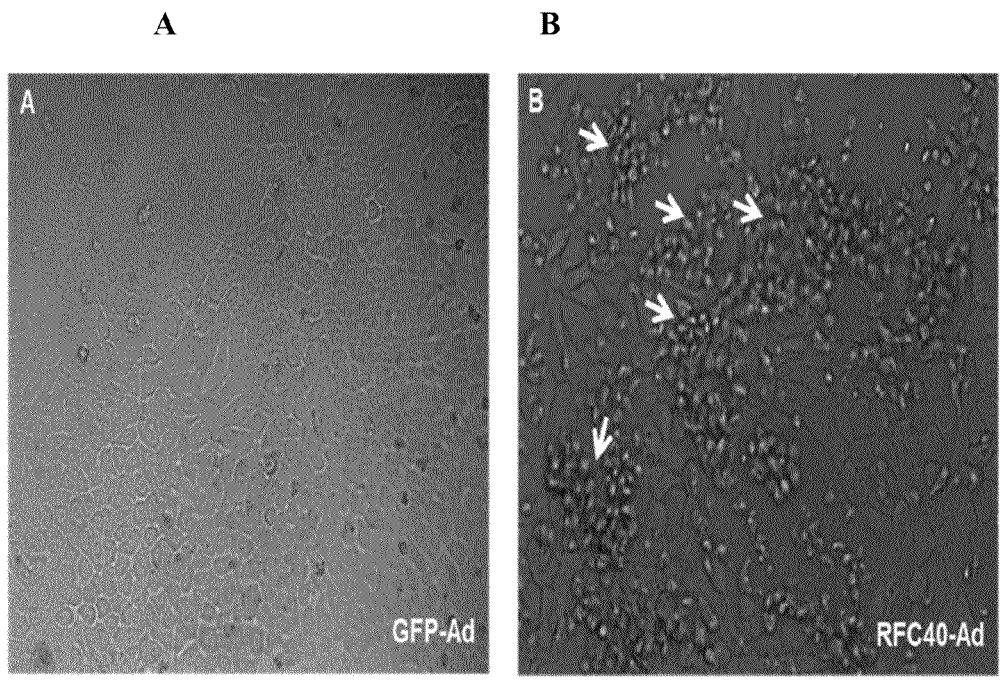
FIGS. 15A and 15B Control (A) and RFC40-Ad (B) transfected MCF10A cells were subjected to DIC microscopy using Nikon Eclipse TE2000-E (20×). Arrows indicate stromal-like phenotype in RFC40-Ad transfected MCF10A cells.
Figure 19:
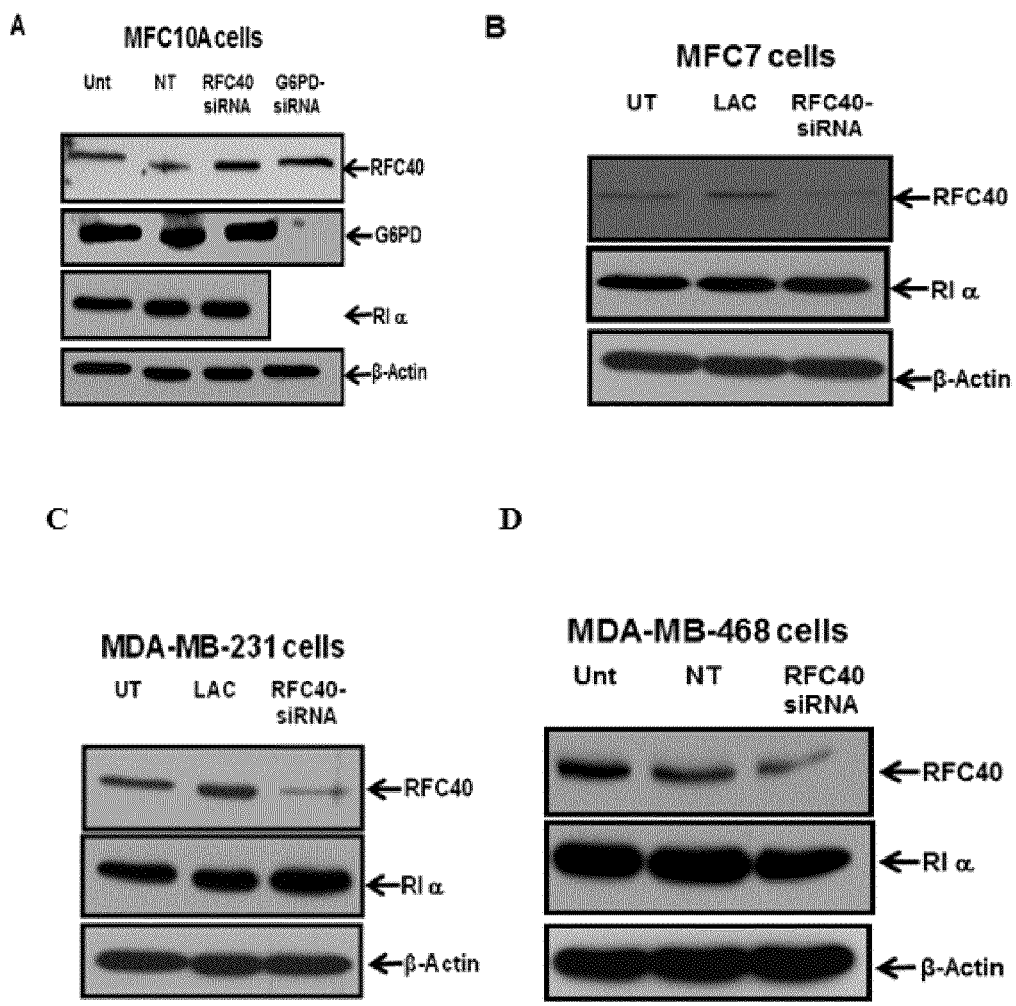
FIG. 19A-19D MCF10A (non-cancerous; A), MCF7 (estrogen positive breast cancer cells; B), MDA-MB-231 (estrogen negative breast cancer cells; C) and MDA-MB-468 (triple negative like breast cancer cells; D) cells were transfected with non-targeting (NT; A & D), Lamin A/C-LAC; B & C), glucose-6-phosphate-dehydrogenase (G6PD; A) and RFC40 siRNA—smartpool (100 nM; cocktail of four different sequences; A-D) as indicated in the figure for 72 hr. Cells lysates were subjected to Western blot analysis using anti-RFC40, anti-RIα and anti-G6PD antibodies, respectively. β-Actin was used as loading control.

We sought to inhibit the endogenous RFC40 gene by transfecting MCF10A, MFC7, MDA-MB-231 and MDA-MB-468 cells with ON-TargetPLUS Smartpool siRNA against RFC40 for 72 hr. The RFC40 mRNA sequence and Smartpool siRNA set of four siRNA sequences are shown in FIG. 15. The Smartpool siRNA (Dharmacon, Inc., TX, USA) is comprised of four RFC40 targeted siRNA sequences (Cat# L-019061-00-0005): RFC40-siRNA-S1 (Cat# J-019061-05), RFC40-siRNA-S2 (Cat# J-019061-06), RFC40-siRNA-S3 (Cat# J-019061-07) and RFC40-siRNA-S4 (Cat# J-019061-08), which targets RFC40-mRNA as shown in FIG. 18. Additionally, cells were also transfected with a scrambled siRNA sequence/non-targeting-siRNA (NT) (Dharmacon, Inc. Tx, USA; Cat# D-001210-02-05), that does not target for any known human genes as a negative control as shown in FIG. 18.

siRNA transfection Protocol: MCF10A (non-cancerous; FIG. 19A), MCF7 (estrogen positive breast cancer cells; FIG. 19B), MDA-MB-231 (estrogen negative breast cancer cells; FIG. 19C) and MDA-MB-468 (TNBC cells; FIG. 19D) cells were transfected with non targeting (NT; 100 nM; FIGS. 19A & D), Lamin A/C—(LAC; 100 nM; FIGS. 19B & C), glucose-6-phosphate-dehydrogenase (G6PD; 100 nM; FIG. 19A) and RFC40 siRNA—smartpool (100 nM; cocktail of four different sequences; FIG. 19A-D) as indicated in the figure for 72 hr using 2.5 µl of Dharmafect Reagent 1 (Dharmacon, Inc., TX, USA). Cells lysates were subjected to Western blot analysis using anti-RFC40, anti-RIα (Pharmingen, Inc., CA, USA) and anti-G6PD (Santa Cruz, Calif., USA) antibodies, respectively. β-Actin was used as loading control.

Remarkably, we found that endogenous RFC40 protein was not knocked-down in MCF10A cells (FIG. 19A). To confirm that the MCF10A cells were accessible to the siRNA and the transfection reagent, we transfected MCF10A cells with an on-target siRNA against a house-keeping gene, Glucose-6 phosphate dehydrogenase (G6PD) for 72 hr using identical experimental conditions as RFC40-SiRNA. We observed almost 90-95% knock-down of G6PD protein in MCF10A cells (FIG. 19A). Furthermore, RFC40 protein was approximately 85-90% knocked-down in estrogen positive breast cancer cells (MCF7) and estrogen negative breast cancer cells (MDA-MB-231) (FIGS. 19B and C). Similar specific knock down of RFC40 was observed MDA-MB-468 cells (FIG. 19D), suggesting that RFC40 gene/protein was selectively not knocked-down only in the cancerous cells.

Figure 20:
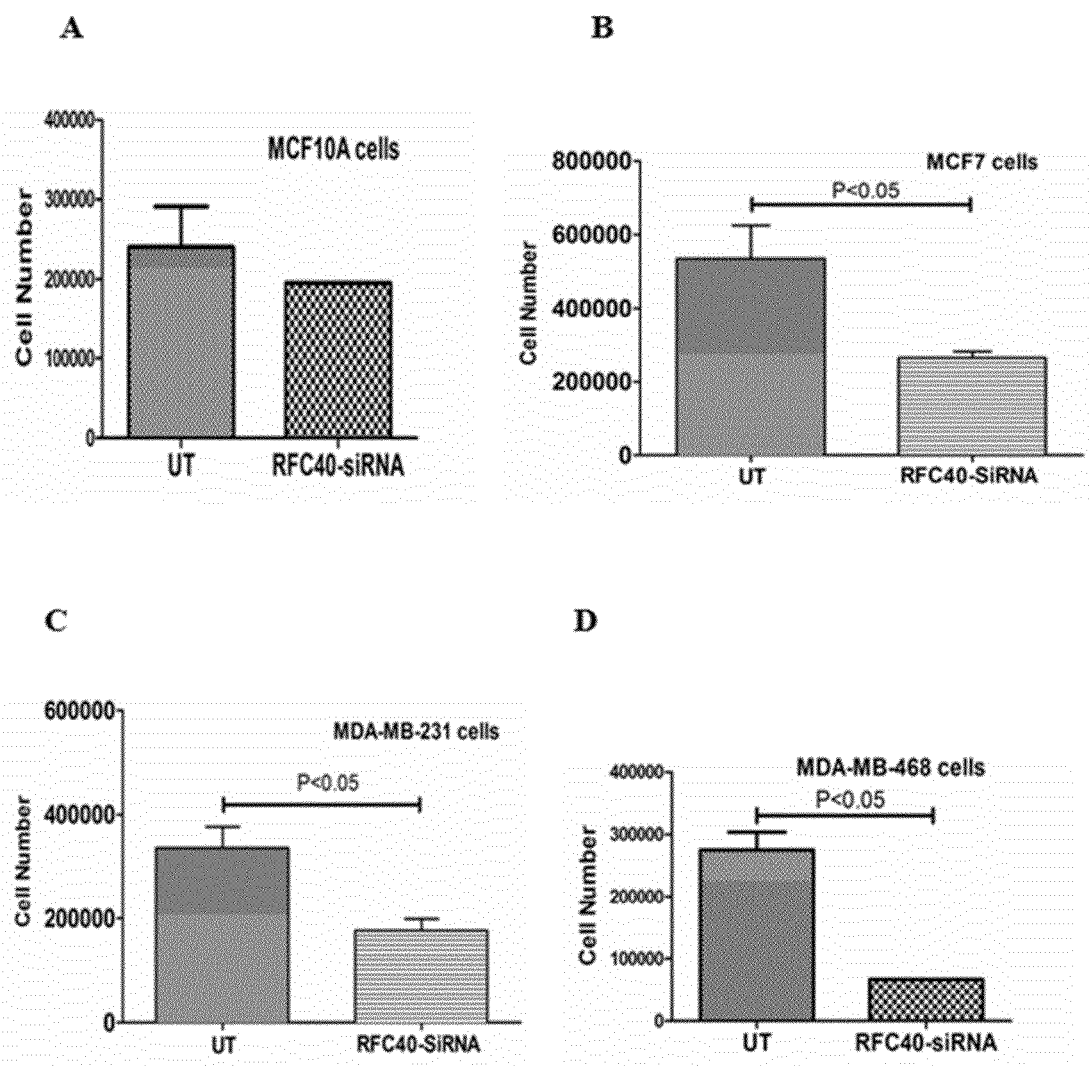
FIG. 20A-20D MCF10A, MCF7, MDA-MB-231 and MDA-MB-468 cells were transfected with Smartpool RFC40-SiRNA (100 nM) for 72 hr. The cells were trypsinized, resuspended in 1×PBS and counted using a hemocytometer. Graph represents the number of MCF10A (A; n=4)) MCF7 (B; n=3), MDA-MB-231 (C; n=3) and MDA-MB-468 (D; n=3) cells vs the untransfected (UT) and RFC40-siRNA treated cells.

Furthermore, before lysing the cells we performed cell count analyses using hemocytometer on all the cell types. The number of each of the cancerous MCF7, MDA-MB-231 and MDA-MB-468 cells was significantly reduced in siRNA treated versus untreated conditions (FIG. 20), for example the number of MDA-MB-468 cells was reduced by approximately 60% in the RFC40-siRNA treated cells as compared to those treated with NT (FIG. 20D), suggesting that inhibition of endogenous RFC40 resulted in cell death. In striking contrast, there was minimal reduction in the cell numbers in the RFC40-siRNA treated noncancerous MCF10A cells as compared to those treated with UT (FIG. 20A).

We next incubated untransfected (Unt), NT and RFC40-siRNA treated cells with Hoechst 33342 that binds to the DNA, for 45 min at 37° C. and performed immunofluorescent microscopy (at 20×). We found several apoptotic nuclei in the RFC40-siRNA treated MDA-MB-468 cells (FIG. 21B) as compared to NT or Unt, however, no such apoptotic nuclei was observed in the RFC40-siRNA treated MCF10A cells (FIG. 21A), suggesting that cell death occurred, and may be due to apoptosis, only in the MDA-MB-468 cells, after RFC40-SiRNA treatment. This data indicates that effective targeting of RFC40 occurs selectively only in the cancerous cells and not the normal cells.

To further evaluate the siRNA sequences against RFC40, normal and breast cancer cell lines were transfected with individual siRNAs from the On-Targetplus-Smartpool selection, particularly with a single siRNA and particularly either of RFC40-siRNA-S1, RFC40-siRNA-S2, RFC40-siRNA-S3, or RFC40-siRNA-S4, using the transfection protocol as described above. MCF10A and MDA-MB-231 cells were transfected with RFC40-SiRNA-S1/S2/S3/S4 (100 nM) for 72 hr and RFC40 protein expression was assessed by Western blot analyses RFC40 protein was significantly reduced by S1, S2, S3 and S4 siRNA in MDA-MB-231 cells as compared to that in MCF10A cells (FIG. 22). The β-Actin control was unchanged.

Similar experiments were conducted with individual siRNAs S1, S2, S3 and S4 on MCF10A and MDA-MB-231 cells. Cell number analysis was performed using Cyquant cell number analyses kit. The results are depicted in FIG. 23. The graphs represent the number of MCF10A (FIG. 23A; n=8) and MDA-MB-231 (FIG. 23B; n=8) cells versus the untransfected (UT) and RFC40-siRNA-S1/S2/S3/S4 treated cells. No significant effect to reduce cell number was seen in normal MCF10A cells, in fact siRNA S4 appeared to increase cell number somewhat. In contrast, reduction of cell numbers in estrogen negative breast cancer cells MDA-MB-231 cells by each of S2, S3 and S4 was statistically significant.

Example 7 miR Studies

To further assess RFC40 inhibition via another approach, studies were undertaken with miRNA (microRNA, miR). Human miR-hsa-125a-3p aligns with RFC2 (RFC40) sequence (see alignment in FIG. 24) with a mirSVR score of −0.1347 or −0.14 and is listed as a mRNA targeted by hsa-miR-125a-3p, along with numerous other mRNAs in microRNA.org. The microRNA.org site lists over 9,000 mRNA predicted targets for miR-hsa-125a-3p, with scores starting at −2.97 ranging down to −0. No validated targets are listed. MicroRNA target predictions utilize recognized and published methods (Betel, D. et al (2010) Genome Biology 11:R90; Betel, D et al (2008) Nucl Acids Res 36:D149-53; John, B et al (2005) PLoS Biol 3(7):e264). Another microRNA website, the miRDB site, provides 295 predicted target mRNAs and RFC40 (RFC2) is not among the predicted targets. There is no report of any specific effect or activity of miR-hsa-125a-3p against RFC40. Activity would not be predicted as significant, particularly given the mirSVR score, and that there are many other targets with higher relative scores. The miR-hsa-125a-3p sequence is 5'ACAGGUGAG-GUUCUUGGGAGCC3' (SEQ ID NO:7) (Dharmacon, Inc. TX, USA; Cat# C-301060-01-0005).

To determine miR-hsa-125a-3p activity against RFC40, human MFC10A and MDA-MB-231 cells were transfected with miRNA negative control #1-(Accession no. MI0000315; Dharmacon, Inc., TX, USA; Cat# CN-002000-01-05) and miR-hsa-125a-3p (100 nM) for 72 hrs. Effects on RFC40 protein levels was determined by Western blot analysis using anti-RFC40 antibody. β-Actin was used as a loading control. RFC40 protein was reduced after transfection of miR-hsa-125a-3p, but not affected in untreated or miRNA negative control#1 treated MDA-MB-231 cells (FIG. 25). No change or difference was observed in MCF10A cells.

Similarly, human MFC10A and MDA-MB-231 cells transfected with miRNA negative control #1 and miR-hsa-125a-3p (100 nM) for 72 hrs were trypsinized, resuspended in 1×PBS and counted using a hemocytometer. Cell number was determined for miR treated and untreated cells and is graphed in FIG. 26. The cell number of MCF10A cells was not significantly different in miR treated versus untreated conditions. However, cell number of MDA-MB-231 (estrogen (ER) negative breast cancer) cells significantly decreased on treatment with miR-hsa-125a-3p (FIG. 26).

In order to alter the complementarity of an RFC40 targeted miRNA and further test on-target effects, alternative miRs have been designed showing improved and reduced complementarity for RFC40 (RFC2). Modified alignments and sequences are depicted in FIG. 24. An exemplary improved miR is provided in ACAGGUGAUCCACUUGGGAGCC (modified miR#1 FIG. 24) (SEQ ID NO:8).

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A pharmaceutical composition for use in prophylaxis and/or therapy of cancer, the composition comprising a pharmaceutically acceptable carrier and an isolated polynucleotide, wherein the polynucleotide is selected from the group consisting of: (a) a microRNA comprising the sequence of SEQ ID NO:8, (b) a microRNA comprising the sequence of SEQ ID NO:9, (c) a short-hairpin RNA (shRNA) comprising the sequence of SEQ ID NO:15, (d) a shRNA comprising the sequence of SEQ ID NO:16, and combinations thereof.

2. The pharmaceutical composition of claim 1, wherein the isolated polynucleotide is the isolated microRNA comprising the sequence of SEQ ID NO:8 or the isolated microRNA comprising the sequence of SEQ ID NO:9.

3. The pharmaceutical composition of claim 1, wherein the isolated polynucleotide consists of a sequence selected from the sequence of SEQ ID NO:8 and the sequence of SEQ ID NO:9.

4. The pharmaceutical composition of claim 1, wherein the pharmaceutical composition is in a sealed container in an article of manufacture, wherein the article of manufacture comprises printed material, wherein the printed material provides an indication that the pharmaceutical composition is for prophylaxis and/or therapy of cancer, and wherein the indication is that the pharmaceutical composition is for prophylaxis and/or therapy of estrogen positive, or estrogen negative, or progesterone/estrogen/HER2 negative breast cancer.

5. The pharmaceutical composition of claim 1, wherein the isolated polynucleotide is the shRNA comprising the sequence of SEQ ID NO:15.

6. The pharmaceutical composition of claim 1, wherein the isolated polynucleotide is the shRNA comprising the sequence of SEQ ID NO:16.

\* \* \* \* \*

SEQUENCE LISTING

<160> NUMBER OF SEQ ID NOS: 17

<210> SEQ ID NO 1
<211> LENGTH: 354
<212> TYPE: PRT
<213> ORGANISM: Human

<400> SEQUENCE: 1

Met Glu Val Glu Ala Val Cys Gly Gly Ala Gly Val Glu Ala Gln
1               5                   10                  15

Asp Ser Asp Pro Ala Pro Ala Phe Ser Lys Ala Pro Gly Ser Ala Gly
            20                  25                  30

His Tyr Glu Leu Pro Trp Val Glu Lys Tyr Arg Pro Val Lys Leu Asn
                35                  40                  45

Glu Ile Val Gly Asn Glu Asp Thr Val Ser Arg Leu Glu Val Phe Ala
            50                  55                  60

Arg Glu Gly Asn Val Pro Asn Ile Ile Ile Ala Gly Pro Pro Gly Thr
65                  70                  75                  80

Gly Lys Thr Thr Ser Ile Leu Cys Leu Ala Arg Ala Leu Leu Gly Pro
                85                  90                  95

Ala Leu Lys Asp Ala Met Leu Glu Leu Asn Ala Ser Asn Asp Arg Gly
            100                 105                 110

Ile Asp Val Val Arg Asn Lys Ile Lys Met Phe Ala Gln Gln Lys Val
            115                 120                 125

Thr Leu Pro Lys Gly Arg His Lys Ile Ile Leu Asp Glu Ala Asp
            130                 135                 140

Ser Met Thr Asp Gly Ala Gln Gln Ala Leu Arg Arg Thr Met Glu Ile
145                 150                 155                 160

Tyr Ser Lys Thr Thr Arg Phe Ala Leu Ala Cys Asn Ala Ser Asp Lys
                165                 170                 175

Ile Ile Glu Pro Ile Gln Ser Arg Cys Ala Val Leu Arg Tyr Thr Lys
            180                 185                 190

Leu Thr Asp Ala Gln Ile Leu Thr Arg Leu Met Asn Val Ile Glu Lys
            195                 200                 205

Glu Arg Val Pro Tyr Thr Asp Asp Gly Leu Glu Ala Ile Ile Phe Thr
210                 215                 220

Ala Gln Gly Asp Met Arg Gln Ala Leu Asn Asn Leu Gln Ser Thr Phe
225                 230                 235                 240

Ser Gly Phe Gly Phe Ile Asn Ser Glu Asn Val Phe Lys Val Cys Asp
                245                 250                 255

Glu Pro His Pro Leu Leu Val Lys Glu Met Ile Gln His Cys Val Asn
            260                 265                 270

Ala Asn Ile Asp Glu Ala Tyr Lys Ile Leu Ala His Leu Trp His Leu
            275                 280                 285

Gly Tyr Ser Pro Glu Asp Ile Ile Gly Asn Ile Phe Arg Val Cys Lys
            290                 295                 300

Thr Phe Gln Met Ala Glu Tyr Leu Lys Leu Glu Phe Ile Lys Glu Ile
305                 310                 315                 320

Gly Tyr Thr His Met Lys Ile Ala Glu Gly Val Asn Ser Leu Leu Gln
                325                 330                 335

Met Ala Gly Leu Leu Ala Arg Leu Cys Gln Lys Thr Met Ala Pro Val
            340                 345                 350

Ala Ser

```
<210> SEQ ID NO 2
<211> LENGTH: 1066
<212> TYPE: DNA
<213> ORGANISM: human

<400> SEQUENCE: 2
atggaggtgg aggccgtctg tggtggcgcg ggcgaggtgg aggcccagga ctctgaccct      60
gcccctgcct tcagcaaggc ccccggcagc gccggccact acgaactgcc gtgggttgaa     120
aaatataggc cagtaaagct gaatgaaatt gtcgggaatg aagacaccgt gagcaggcta     180
gaggtctttg caagggaagg aaatgtgccc aacatcatca ttgcgggccc tccaggaacc     240
ggcaagacca caagcattct gtgcttggcc cgggccctgc tgggcccagc actcagaaga     300
tgccatgttg gaactcaatg cttcaaatga cggggcatt gacgttgtga ggaataaaat     360
taaaatgttt gctcaacaaa aagtcactct tcccaaaggc cgacataaga tcatcattct     420
ggatgaagca gacagcatga ccgacggagc ccagcaagcc ttgaggagaa ccatggaaat     480
ctactctaaa accactcgct cgcccttgc ttgtaatgct tcggataaga tcatcgagcc     540
cattcagtcc cgctgtgcag tcctccggta cacaaagctg accgacgccc agatcctcac     600
caggctgatg aatgttatcg agaaggagag ggtaccctac actgatgacg cctagaagc     660 catcatcttc acggcccagg gagacatgag gcaggcgctg aacaacctgc agtccacctt     720
ctcaggattt ggcttcatta acagtgagaa cgtgttcaag gtctgtgacg agccccaccc     780
actgctggta aaggagatga tccagcactg tgtgaatgcc aacattgacg aagcctacaa     840
gattcttgct cacttgtggc atctgggcta ctcaccagaa gatatcattg gcaacatctt     900
tcgagtgtgt aaaactttcc aaatggcaga atacctgaaa ctggagtttta tcaaggaaat     960 tggatacact cacatgaaaa tagcggaagg agtgaactct cttttgcaga tggcaggcct    1020
cctggcaagg ctgtgtcaga agacaatggc cccggtggcc agttag                   1066

<210> SEQ ID NO 3
<211> LENGTH: 19
<212> TYPE: RNA
<213> ORGANISM: artificial sequence
<220> FEATURE:
<223> OTHER INFORMATION: siRNA

<400> SEQUENCE: 3
cuuguaaugc uucggauaa                                                    19

<210> SEQ ID NO 4
<211> LENGTH: 19
<212> TYPE: RNA
<213> ORGANISM: artificial sequence
<220> FEATURE:
<223> OTHER INFORMATION: siRNA

<400> SEQUENCE: 4
gaacugccgu ggguugaaa                                                    19

<210> SEQ ID NO 5
<211> LENGTH: 19
<212> TYPE: RNA
<213> ORGANISM: artificial sequence
<220> FEATURE:
<223> OTHER INFORMATION: SiRNA

<400> SEQUENCE: 5
cggcaagacc acaagcauu                                                    19
```

```
<210> SEQ ID NO 6
<211> LENGTH: 19
<212> TYPE: RNA
<213> ORGANISM: artificial sequence
<220> FEATURE:
<223> OTHER INFORMATION: SiRNA

<400> SEQUENCE: 6
gcugugcagu ccuccggua                                                   19

<210> SEQ ID NO 7
<211> LENGTH: 22
<212> TYPE: RNA
<213> ORGANISM: human

<400> SEQUENCE: 7
acaggugagg uucuugggag cc                                               22

<210> SEQ ID NO 8
<211> LENGTH: 22
<212> TYPE: RNA
<213> ORGANISM: artificial sequence
<220> FEATURE:
<223> OTHER INFORMATION: Modified miR

<400> SEQUENCE: 8
acaggugauc cacuugggag cc                                               22

<210> SEQ ID NO 9
<211> LENGTH: 22
<212> TYPE: RNA
<213> ORGANISM: artificial sequence
<220> FEATURE:
<223> OTHER INFORMATION: modified miRNA

<400> SEQUENCE: 9
acaggugagg auaacaggag cc                                               22

<210> SEQ ID NO 10
<211> LENGTH: 22
<212> TYPE: DNA
<213> ORGANISM: artificial sequence
<220> FEATURE:
<223> OTHER INFORMATION: PCR primer

<400> SEQUENCE: 10
atggaggtgg aggccgtctg tg                                               22

<210> SEQ ID NO 11
<211> LENGTH: 25
<212> TYPE: DNA
<213> ORGANISM: artificial sequence
<220> FEATURE:
<223> OTHER INFORMATION: PCR primer

<400> SEQUENCE: 11
cctctagcct gctcacggtg tcttc                                            25

<210> SEQ ID NO 12
<211> LENGTH: 24
<212> TYPE: DNA
<213> ORGANISM: artificial sequence
<220> FEATURE:
<223> OTHER INFORMATION: PCR primer

<400> SEQUENCE: 12
```

```
ctcatgacca cagtccatgc catc                                              24

<210> SEQ ID NO 13
<211> LENGTH: 20
<212> TYPE: DNA
<213> ORGANISM: artificial sequence
<220> FEATURE:
<223> OTHER INFORMATION: PCR primer

<400> SEQUENCE: 13
cggaaggcca tgccagtgag                                                   20

<210> SEQ ID NO 14
<211> LENGTH: 19
<212> TYPE: RNA
<213> ORGANISM: artificial sequence
<220> FEATURE:
<223> OTHER INFORMATION: SiRNA

<400> SEQUENCE: 14
uaaggcuaug aagagauac                                                    19

<210> SEQ ID NO 15
<211> LENGTH: 29
<212> TYPE: RNA
<213> ORGANISM: artificial sequence
<220> FEATURE:
<223> OTHER INFORMATION: shRNA

<400> SEQUENCE: 15
acuacgaacu gccguggguu gaaaaauau                                         29

<210> SEQ ID NO 16
<211> LENGTH: 29
<212> TYPE: RNA
<213> ORGANISM: artificial sequence
<220> FEATURE:
<223> OTHER INFORMATION: shRNA

<400> SEQUENCE: 16
gucccgcugu gcaguccucc gguacacaa                                         29

<210> SEQ ID NO 17
<211> LENGTH: 22
<212> TYPE: RNA
<213> ORGANISM: human
<220> FEATURE:
<223> OTHER INFORMATION: RFC2-mRNA-3'UTR

<400> SEQUENCE: 17
ccgaggcagg uggaucaccu ga                                                22
```